US012637472B2

(12) United States Patent
Wu et al.

(10) Patent No.: US 12,637,472 B2
(45) Date of Patent: May 26, 2026

(54) BENZIMIDAZOLE HETEROATOM-CONTAINING SPIRO COMPOUND AND MEDICINAL USE THEREOF

(71) Applicant: Changzhi University, Changzhi (CN)

(72) Inventors: Lintao Wu, Changzhi (CN); Xumei Zheng, Changzhi (CN); Zhijun Wang, Changzhi (CN); Chun Han, Changzhi (CN); Wei Gao, Changzhi (CN); Chaohua Guo, Changzhi (CN)

(73) Assignee: Changzhi University, Changzhi (CN)

( * ) Notice: Subject to any disclaimer, the term of this patent is extended or adjusted under 35 U.S.C. 154(b) by 320 days.

(21) Appl. No.: 18/619,219

(22) Filed: Mar. 28, 2024

(65) Prior Publication Data

US 2025/0215000 A1 Jul. 3, 2025

(30) Foreign Application Priority Data

Dec. 27, 2023 (CN) ......................... 202311816053.6

(51) Int. Cl.

| | |
|---|---|
| ***C07D 487/04*** | (2006.01) |
| ***A61K 31/4184*** | (2006.01) |
| ***A61P 35/00*** | (2006.01) |
| ***C07D 403/06*** | (2006.01) |
| ***C07D 403/14*** | (2006.01) |

(52) U.S. Cl.

CPC ........ *C07D 487/04* (2013.01); *A61K 31/4184* (2013.01); *A61P 35/00* (2018.01); *C07D 403/06* (2013.01); *C07D 403/14* (2013.01)

(58) Field of Classification Search

CPC ... C07D 487/04; C07D 403/06; C07D 403/14
See application file for complete search history.

(56) References Cited

PUBLICATIONS

Poornachandran, et al. Synthetic Communications, 36: 141-150, 2006.*

* cited by examiner

*Primary Examiner* — Shawquia Jackson
(74) *Attorney, Agent, or Firm* — Bayramoglu Law Offices LLC

(57) ABSTRACT

A benzimidazole heteroatom-containing spiro compound and a medicinal use thereof are provided. Activity test results show that the benzimidazole heteroatom-containing spiro compound provided by the present disclosure has a significant antiproliferative activity for human liver tumor cells HepG2, human colon cancer cells HCT116, and/or human gastric adenocarcinoma cells AGS, and most of the compounds involved in the present disclosure exhibit a stronger antiproliferative activity than cisplatin and/or Nutlin-3a. Therefore, the benzimidazole heteroatom-containing spiro compound provided by the present disclosure has a prospect of being developed into an antitumor drug, such as for liver cancer, colon cancer, or gastric cancer.

5 Claims, No Drawings

BENZIMIDAZOLE HETEROATOM-CONTAINING SPIRO COMPOUND AND MEDICINAL USE THEREOF

CROSS REFERENCE TO THE RELATED APPLICATIONS

This application is based upon and claims priority to Chinese Patent Application No. 202311816053.6, filed on Dec. 27, 2023, the entire contents of which are incorporated herein by reference.

TECHNICAL FIELD

The present disclosure belongs to the field of pharmaceutical chemistry, and specifically relates to a benzimidazole heteroatom-containing spiro compound and a medicinal use thereof.

BACKGROUND

Cancer has become a leading cause of death worldwide, second only to heart disease. The incidence and mortality of cancer continue to increase. Cancer seriously threatens human life and health. Cancer develops rapidly and can invade and spread to surrounding tissues. Thus, cancer is extremely destructive. In addition to causing obstruction and compression in the body, cancer may affect the normal function of body organs and cause death. With the rapid development of science and technology in this era, cancer has undoubtedly become a great threat to human life. Cancer continues to bring huge health and emotional burdens to individuals and societies. As China gradually enters an aging society, the number of cancer patients is bound to increase. Therefore, the development of small-molecule drugs for treating various cancer cells is of great practical significance.

SUMMARY

An objective of the present disclosure is to provide a benzimidazole heteroatom-containing spiro compound and a medicinal use thereof.

The objective of the present disclosure is allowed by the following technical solutions:

A benzimidazole heteroatom-containing spiro compound with the following chemical structure or a pharmaceutically acceptable salt thereof is provided:

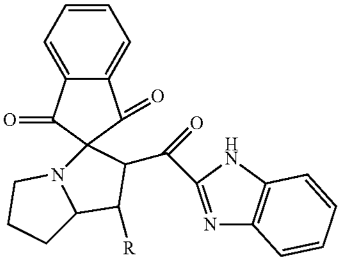

-continued

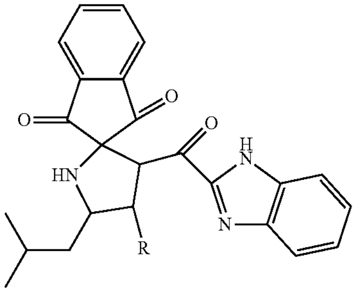

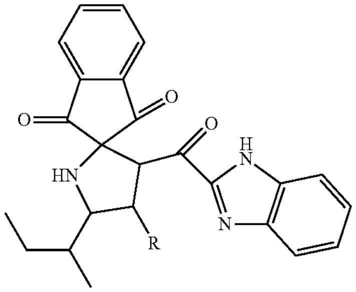

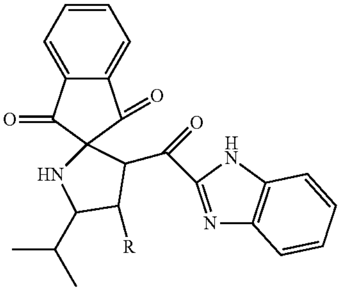

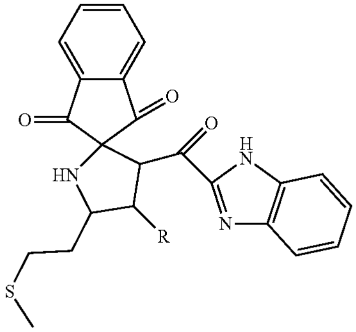

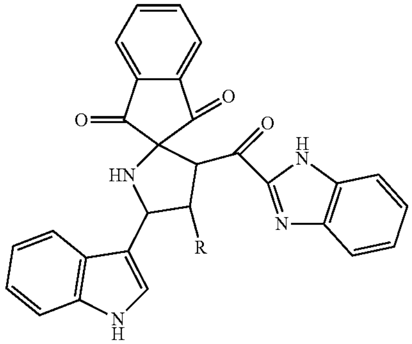

where R is selected from the following structures:

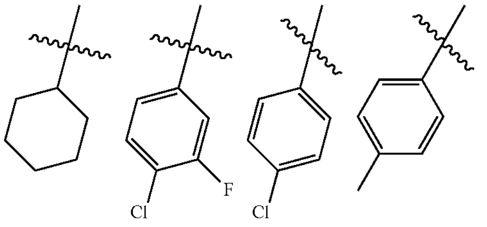

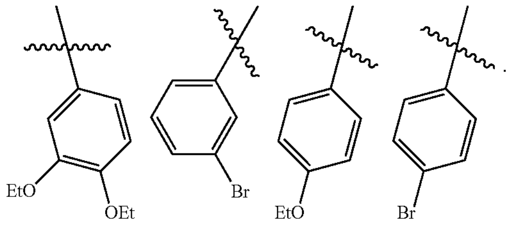

A medicinal use of the benzimidazole heteroatom-containing spiro compound or the pharmaceutically acceptable salt thereof in preparation of an antitumor drug is provided.

Further, a tumor is liver cancer.

Further, a tumor is colon cancer.

Further, a tumor is gastric cancer.

A method of treating a tumor is provided, including orally administrating or injecting a drug to a tumor patient, where an active ingredient of the drug is the benzimidazole heteroatom-containing spiro compound or the pharmaceutically acceptable salt thereof.

Further, a tumor is liver cancer.

Further, a tumor is colon cancer.

Further, a tumor is gastric cancer.

Beneficial Effects

The benzimidazole heteroatom-containing spiro compound provided by the present disclosure has a significant antiproliferative activity for human liver tumor cells HepG2, human colon cancer cells HCT116, and/or human gastric adenocarcinoma cells AGS, and most of the compounds involved in the present disclosure exhibit a stronger antiproliferative activity than cisplatin and/or Nutlin-3a. Therefore, the benzimidazole heteroatom-containing spiro compound provided by the present disclosure has a prospect of being developed into an antitumor drug, such as for liver cancer, colon cancer, or gastric cancer.

DETAILED DESCRIPTION OF THE EMBODIMENTS

Example 1

Compound 1: 2-(1H-benzimidazol-2-carbonyl)-1-cyclohexyl-1,2,5,6,7,7a-hexahydrospiroinden-2,3-pyrrolizine-1,3-dione

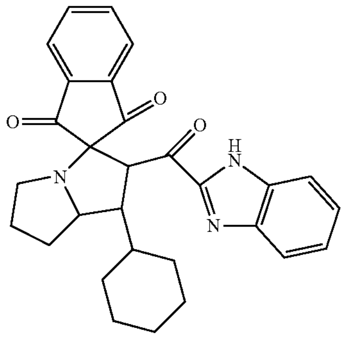 [SMILES: O=C(c1nc2ccccc2[nH]1)C1C(C2CCCCC2)C2CCCN2C12C(=O)c1ccccc1C2=O]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 336 mg (3 mmol) of cyclohexanecarboxaldehyde was added to the flask to allow a reaction for 8 h to obtain a reaction solution;

monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 580 mg of a product: 1-(1H-benzimidazol-2-yl)-3-cyclohexylprop-2-en-1-one. 142 mg (0.56 mmol) of the 1-(1H-benzimidazol-2-yl)-3-cyclohexylprop-2-en-1-one, 119 mg (0.67 mmol) of ninhydrin hydrate, and 64 mg (0.56 mmol) of proline were weighed and added to a reaction flask, 5 mL of a methanol aqueous solution (methanol:water=10:1) was added to the reaction flask, and a reaction was allowed at room temperature for 2 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 120 mg of a yellow solid, and a melting point of the yellow solid was measured by a micro melting point meter to be 240.0° C. to 243.0° C. $^1$H NMR (400 MHz, DMSO): δ 13.25 (s, 1H, NH), 7.98, 7.96 (s, 2H, ArH) 7.93, 7.91 (s, 2H, ArH), 7.60 (s, 2H, ArH), 7.14 (s, 2H, ArH), 7.12, 7.09, 3.65 (d, 1H, CH), 2.67, 2.64 (s, 2H, $CH_2$), 2.29 (m, 1H, CH), 1.92-1.13 (m, 16H, $CH_2$).

Compound 2: 2-(1H-benzimidazol-2-carbonyl)-1-(3-fluoro-4-chlorophenyl)-1,2,5,6,7,7a-hexahydrospiro[inden-2,3-pyrrolizine]-1,3-dione

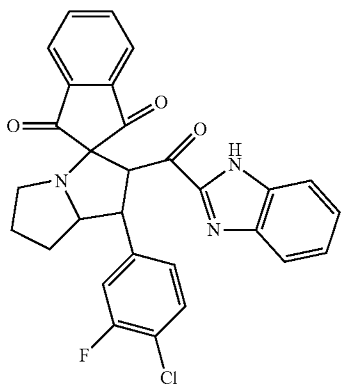 [SMILES: O=C(c1nc2ccccc2[nH]1)C1C(c2ccc(Cl)c(F)c2)C2CCCN2C12C(=O)c1ccccc1C2=O]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 475 mg (3 mmol) of 3-fluoro-4-chlorobenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 823 mg of a product: (E)-1-(1H-benzo[d]imidazol-2-yl)-3-(3-fluoro-4-chlorophenyl)prop-2-en-1-one. 5 mL of a methanol solution (MeOH:$H_2O$=10:1) was first added to a reaction flask, then 168 mg (0.56 mmol) of the (E)-1-(1H-benzo[d]imidazol-2-yl)-3-(3-fluoro-4-chlorophenyl)prop-2-en-1-one, 119 mg (0.67 mmol) of ninhydrin hydrate, and 64 mg (0.56 mmol) of proline were added successively to the reaction flask, and a reaction was allowed at room temperature for 8 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 105 mg of a yellow solid, and a melting point of the yellow solid was measured by a micro melting point meter to be 219.3° C. to 221.4° C. $^1$H NMR (400 MHz, DMSO): δ 13.26 (s, 1H, NH), 8.21-8.20 (m, 2H, ArH), 8.18-8.16 (m, 2H, ArH), 7.85-7.80 (m, 2H, ArH), 7.62-7.56 (m, 1H, ArH), 7.44-7.25 (m, 2H, ArH), 7.23-7.19 (m, 1H, ArH), 7.02-6.79 (m, 1H, ArH), 3.88-3.81 (d, 1H, CH), 2.83-2.77 (q, 1H, CH), 2.63 (m, 1H, CH), 2.48-2.38 (t, 2H, $CH_2$), 1.97-1.84 (m, 2H, $CH_2$), 1.73-1.19 (m, 2H, $CH_2$).

Compound 3: 2-(1H-benzimidazol-2-carbonyl)-1-4-chlorophenyl-1,2,5,6,7,7a-hexahydrospiroinden-2,3-pyrrolizine-1,3-dione

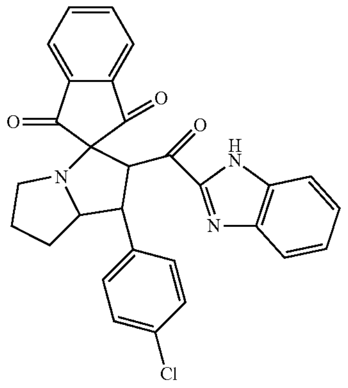 [SMILES: O=C(c1nc2ccccc2[nH]1)C1C(c2ccc(Cl)cc2)C2CCCN2C12C(=O)c1ccccc1C2=O]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 422 mg (3 mmol) of p-chlorobenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 751 mg of a product: (E)-1-(1H-benzo[d]imidazol-2-yl)-3-(4-chlorophenyl)prop-2-en-1-one. 5 mL of absolute ethanol was added to a reaction flask, then 64 mg (0.56 mmol) of proline, 158 mg (0.56 mmol) of the (E)-1-(1H-benzo[d]imidazol-2-yl)-3-(4-chlorophenyl)prop-2-en-1-one, and 119 mg (0.67 mmol) of ninhydrin hydrate were added successively to the reaction flask, and a reaction was allowed for 8 h at room temperature under stirring to obtain a reaction solution; monitoring analysis was conducted by TLC (PE:EA=2:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was concentrated under vacuum to obtain 110 mg of a yellow solid product, and a melting point of the yellow solid product was measured by a micro melting point meter to be 197.0° C. to 199.1° C. $^1H$ NMR (400 MHz, DMSO): δ 13.24 (s, 1H, NH), 8.21-8.18 (m, 2H, ArH), 8.15-7.99 (m, 2H, ArH), 7.84-7.80 (m, 2H, ArH), 7.64-7.56 (m, 2H, ArH), 7.47-7.37 (m, 2H, ArH), 7.25-7.02 (m, 2H, ArH), 3.88-3.78 (d, 1H, CH), 3.31-3.28 (d, 1H, CH), 2.88-2.83 (m, 1H, CH), 2.39-2.36 (t, 2H, $CH_2$), 1.98-1.84 (m, 2H, $CH_2$), 1.74-1.66 (m, 2H, $CH_2$).

Compound 4: 2-(1H-benzimidazol-2-carbonyl)-1-p-tolyl-1,2,5,6,7,7a-hexahydrospiroinden-2,3-pyrrolizine-1,3-dione

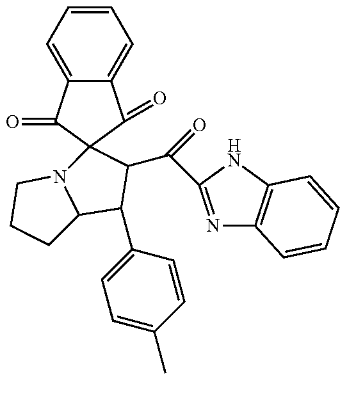 [SMILES: Cc1ccc(C2C3CCCN3C3(C(=O)c4ccccc4C3=O)C2C(=O)c2nc3ccccc3[nH]2)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 360 mg (3 mmol) of p-methylbenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 684 mg of a product: 1-(1H-benzimidazol-2-yl)-3-p-tolylprop-2-en-1-one. 147 mg (0.56 mmol) of the 1-(1H-benzimidazol-2-yl)-3-p-tolylprop-2-en-1-one, 119 mg (0.67 mmol) of ninhydrin hydrate, and 64 mg (0.56 mmol) of proline were weighed, separately; 5 mL of a methanol aqueous solution ($MeOH:H_2O$=10:1) was first added to a reaction flask, then the weighed proline, 1-(1H-benzimidazol-2-yl)-3-p-tolylprop-2-en-1-one, and ninhydrin hydrate were added successively to the reaction flask, and a reaction was allowed under reflux at 80° C. for 2 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 114 mg of a solid, and a melting point of the solid was measured by a micro melting point meter to be 158.2° C. to 159.8° C. $^1H$ NMR (400 MHz, Chloroform-d): δ 10.12 (s, 1H), 8.16-8.11 (m, 1H), 7.79 (td, J=7.4, 1.2 Hz, 1H), 7.60 (td, J=7.4, 1.0 Hz, 1H), 7.55 (dt, J=7.6, 1.1 Hz, 1H), 7.51-7.47 (m, 2H), 7.33-7.28 (m, 1H), 7.26-7.17 (m, 2H), 7.14 (d, J=7.8 Hz, 2H), 7.06-7.02 (m, 2H), 4.99 (d, J=10.6 Hz, 1H), 4.12 (q, J=7.1 Hz, 2H), 3.87 (t, J=10.6 Hz, 1H), 2.30 (s, 3H), 2.04 (s, 2H), 1.29-1.23 (m, 3H).

Compound 5: 2-(1H-benzimidazol-2-carbonyl)-3,4-diethoxyphenyl-1,2,5,6,7,7a-hexahydrospiroinden-2,3-pyrrolizine-1,3-dione

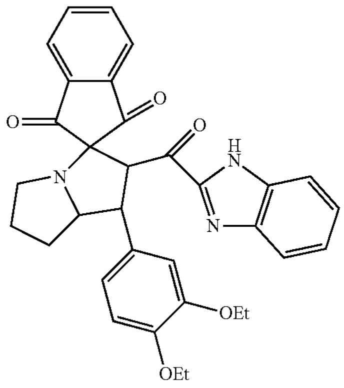 [SMILES: CCOc1ccc(C2C3CCCN3C3(C(=O)c4ccccc4C3=O)C2C(=O)c2nc3ccccc3[nH]2)cc1OCC]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 582 mg (3 mmol) of 3,4-diethoxybenzaldehyde was added to the flask to allow a reaction for 8 h to obtain a reaction solution; monitoring analysis was conducted by TLC, and when a monitoring analysis result showed that the reaction was completed, the reaction solution was poured into a beaker;

an appropriate amount of distilled water was added to the beaker, and the beaker was allowed to stand to make a yellow solid precipitated; and the yellow solid was collected through suction filtration and dried to obtain 890 mg of a product: 1-(1H-benzimidazol-2-yl)-3-(3,4-diethoxyphenyl) prop-2-en-1-one. 5 mL of absolute ethanol was added to a reaction flask, then 64 mg (0.56 mmol) of proline, 188 mg (0.56 mmol) of the 1-(1H-benzimidazol-2-yl)-3-(3,4-diethoxyphenyl)prop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 104 mg of the final product: 2-(1H-benzimidazol-2-carbonyl)-3,4-diethoxyphenyl-1,2,5,6,7,7a-hexahydrospiroinden-2,3-pyrrolizine-1,3-dione, and a melting point of the final product was measured by a micro melting point meter to be 167.9° C. to 170.5° C. $^1$H NMR (400 MHz, DMSO): δ 13.23 (s, 1H, NH), 8.20-8.15 (m, 2H, ArH), 8.11-7.98 (m, 2H, ArH), 7.61-7.60 (m, 2H, ArH), 7.38-7.27 (m, 2H, ArH), 7.22-7.17 (m, 1H, ArH), 7.11-7.02 (m, 1H, ArH), 6.99-6.88 (m, 1H, ArH), 4.13-4.11 (q, 4H, $2CH_2$), 4.08-3.72 (d, 1H, CH), 2.88 (q, 1H, CH), 2.88-2.80 (m, 1H, CH), 2.49-2.39 (t, 2H, $CH_2$), 1.99-1.85 (m, 2H, $CH_2$), 1.73-1.67 (m, 2H, $CH_2$), 1.37-1.14 (t, 6H, $2CH_3$).

Compound 6: 2-(1H-benzimidazol-2-carbonyl)-1-3-bromophenyl-1,2,5,6,7,7a-hexahydrospiroinden-2,3-pyrrolizine-1,3-dione

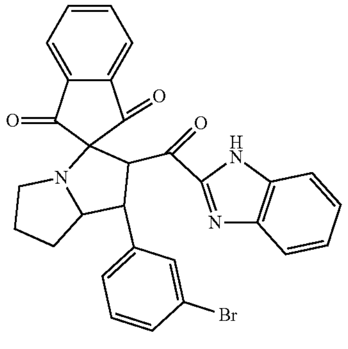 [SMILES: O=C(c1nc2ccccc2[nH]1)C1C(c2cccc(Br)c2)C2CCCN2C12C(=O)c1ccccc1C2=O]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 3-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-3-bromophenylprop-2-en-1-one. 5 mL of absolute ethanol was added to a reaction flask, then 64 mg (0.56 mmol) of proline, 183 mg (0.56 mmol) of the 1-benzimidazol-2-yl-3-bromophenylprop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 124 mg of the final product: 2-(1H-benzimidazol-2-carbonyl)-1-3-bromophenyl-1,2,5,6,7,7a-hexahydrospiroinden-2,3-pyrrolizine-1,3-dione, and a melting point of the final product was measured by a micro melting point meter to be 140.4° C. to 143.0° C. $^1$H NMR (500 MHz, Chloroform-d): δ 8.04 (dd, J=5.7, 3.8 Hz, 2H), 7.90-7.82 (m, 3H), 7.55 (s, 1H), 7.52-7.45 (m, 2H), 7.38 (s, 1H), 7.31-7.23 (m, 2H), 7.04-6.98 (m, 1H), 4.20 (t, J=0.9 Hz, 1H), 3.79 (s, 1H), 3.44 (s, 1H), 2.98 (d, J=9.5 Hz, 1H), 2.90 (d, J=9.5 Hz, 1H), 1.84 (s, 1H), 1.71 (s, 1H), 1.62 (d, J=13.0 Hz, 2H).

Compound 7: 2-(1H-benzimidazol-2-carbonyl)-1-(4-ethoxyphenyl)-1,2,5,6,7,7a-hexahydrospiroinden-2,3-pyrrolizine-1,3-dione

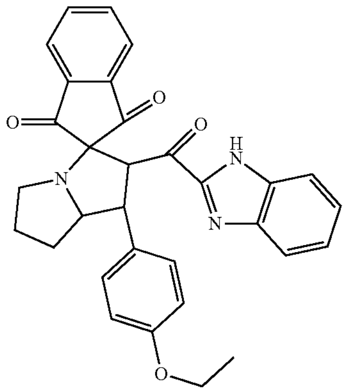 [SMILES: CCOc1ccc(C2C3CCCN3C3(C(=O)c4ccccc4C3=O)C2C(=O)c2nc3ccccc3[nH]2)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 450 mg (3 mmol) of 4-ethoxybenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 890 mg of a product: 1-benzimidazol-2-yl-3-(4-ethoxyphenyl)prop-2-en-1-one. 5 mL of absolute ethanol was added to a reaction flask, then 64 mg (0.56 mmol) of proline, 163 mg (0.56 mmol) of the 1-benzimidazol-2-yl-3-(4-ethoxyphenyl)prop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 104 mg of the final product: 2-(1H-benzimidazol-2-carbonyl)-1-(4-ethoxyphenyl)-1,2,5,6,7,7a-hexahydrospiroinden-2,3-pyrrolizine-1,3-dione, and a melting point of the final product was measured by a micro melting point meter to be 149.5° C. to 151.5° C. $^1$H NMR (500 MHz, Chloroform-d): δ 8.00 (dd, J=5.6, 3.8 Hz, 3H), 7.92-7.82 (m, 4H), 7.56 (s, 1H), 7.37 (s, 1H), 7.25 (s, 1H), 7.15-7.08 (m, 3H), 6.95-6.89 (m, 3H), 4.03 (t, J=1.0 Hz, 1H), 3.97 (s, 2H), 3.79 (s, 1H), 3.57 (s, 1H), 2.98 (d, J=9.5 Hz, 1H), 2.90 (d, J=9.5 Hz, 1H), 1.76 (d, J=18.3 Hz, 2H), 1.64 (s, 1H), 1.60 (s, 1H), 1.40 (s, 3H).

Compound 8: 2-(1H-benzimidazol-2-carbonyl)-1-4-bromophenyl-1,2,5,6,7,7a-hexahydrospiroinden-2,3-pyrrolizine-1,3-dione

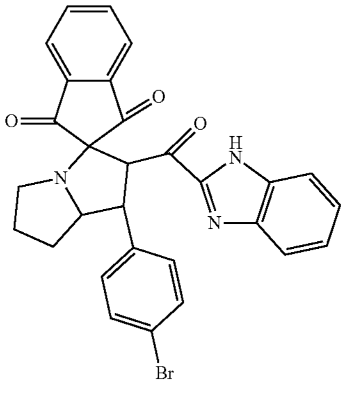 [SMILES: O=C(c1nc2ccccc2[nH]1)C1C(c2ccc(Br)cc2)C2CCCN2C12C(=O)c1ccccc1C2=O]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 4-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-4-bromophenylprop-2-en-1-one. 5 mL of absolute ethanol was added to a reaction flask, then 64 mg (0.56 mmol) of proline, 183 mg (0.56 mmol) of the 1-benzimidazol-2-yl-4-bromophenylprop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 78 mg of the final product: 2-(1H-benzimidazol-2-carbonyl)-1-4-bromophenyl-1,2,5,6,7,7a-hexahydrospiroinden-2,3-pyrrolizine-1,3-dione, and a melting point of the final product was measured by a micro melting point meter to be 201.3° C. to 205.1° C. $^1$H NMR (500 MHz, Chloroform-d): δ 8.04 (dd, J=5.7, 3.8 Hz, 3H), 7.90-7.82 (m, 4H), 7.57-7.51 (m, 4H), 7.38 (s, 1H), 7.25 (s, 1H), 7.18-7.12 (m, 3H), 4.11 (t, J=1.0 Hz, 1H), 3.79 (s, 1H), 3.44 (s, 1H), 2.98 (d, J=9.5 Hz, 1H), 2.90 (d, J=9.5 Hz, 1H), 1.84 (s, 1H), 1.71 (s, 1H), 1.62 (d, J=13.0 Hz, 2H).

Compound 9: 3-(1H-benzimidazol-2-carbonyl)-4-cyclohexyl-5-isobutylspiro[inden-2,2'-pyrrolidine]-1,3-dione

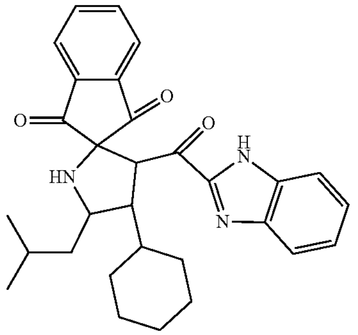 [SMILES: CC(C)CC1NC2(C(=O)c3ccccc3C2=O)C(C(=O)c2nc3ccccc3[nH]2)C1C1CCCCC1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 336 mg (3 mmol) of cyclohexanecarboxaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 580 mg of a product: 1-(1H-benzimidazol-2-yl)-3-cyclohexylprop-2-en-1-one. 5 mL of an ethanol solution was added to a reaction flask, 142 mg (0.56 mmol) of the 1-(1H-benzimidazol-2-yl)-3-cyclohexylprop-2-en-1-one, 119 mg (0.67 mmol) of ninhydrin hydrate, and 73 mg (0.56 mmol) of leucine were added to the reaction flask, and a reaction was allowed at room temperature for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 140 mg of a yellow solid, and a melting point of the yellow solid was measured by a micro melting point meter to be 107.5° C. to 109.5° C. $^1$H NMR (400 MHz, DMSO-$d_6$): δ 13.24 (s, 1H), 8.04 (d, J=7.6 Hz, 1H), 7.91 (td, J=7.5, 1.1 Hz, 1H), 7.69 (td, J=7.5, 1.1 Hz, 1H), 7.39 (t, J=8.0 Hz, 2H), 7.29-7.19 (m, 1H), 7.10-7.01 (m, 1H), 6.93 (d, J=8.0 Hz, 1H), 4.30 (d, J=8.8 Hz, 1H), 3.51 (s, 1H), 1.76 (d, J=12.6 Hz, 1H), 1.69-1.06 (m, 15H), 0.87 (t, J=6.1 Hz, 6H).

Compound 10: 3-(1H-benzimidazol-2-carbonyl)-4-(3-fluoro-4-chlorophenyl)-5-isobutylspiro[inden-2,2'-pyrrolidine]-1,3-dione

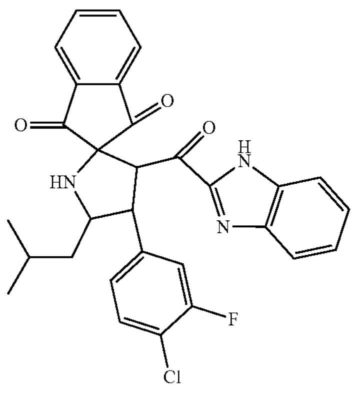 [SMILES: CC(C)CC1NC2(C(=O)c3ccccc3C2=O)C(C(=O)c2nc3ccccc3[nH]2)C1c1ccc(Cl)c(F)c1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl$:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 475 mg (3 mmol) of 3-fluoro-4-chlorobenzaldehyde was added to the flask to allow a reaction for 10 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 812 mg of a product: (E)-1-(1H-benzo[d]imidazol-2-yl)-3-(3-fluoro-4-chlorophenyl)prop-2-en-1-one. 168 mg (0.56 mmol) of the (E)-1-(1H-benzo[d]imidazol-2-yl)-3-(3-fluoro-4-chlorophenyl)prop-2-en-1-one, 119 mg (0.67 mmol) of ninhydrin hydrate, and 73 mg (0.56 mmol) of leucine were weighed, separately; 5 mL of absolute ethanol was first added to a reaction flask, then the weighed leucine, (E)-1-(1H-benzo[d]imidazol-2-yl)-3-(3-fluoro-4-chlorophenyl)prop-2-en-1-one, and ninhydrin hydrate were added successively to the reaction flask, and a reaction was allowed under reflux at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 118 mg of a solid, and a melting point of the solid was measured by a micro melting point meter to be 179.5° C. to 180.2° C. $^1$H NMR (400 MHz, DMSO-$d_6$): δ 13.24 (s, 1H), 8.22-8.17 (m, 1H), 8.01 (td, J=7.5, 1.1 Hz, 1H), 7.76 (td, J=7.5, 1.0 Hz, 1H), 7.61 (t, J=8.1 Hz, 1H), 7.52-7.46 (m, 2H), 7.40-7.34 (m, 2H), 7.26-7.17 (m, 1H), 7.06-6.97 (m, 1H), 6.71 (d, J=8.2 Hz, 1H), 4.50 (d, J=9.6 Hz, 1H), 3.56 (d, J=9.4 Hz, 2H), 3.34 (s, 1H), 1.50-1.38 (m, 1H), 1.31-1.23 (m, 2H), 0.76 (d, J=6.6 Hz, 3H), 0.72 (d, J=6.5 Hz, 3H).

Compound 11: 3-(1H-benzimidazol-2-carbonyl)-4-(4-chlorophenyl)-5-isobutylspiro[inden-2,2'-pyrrolidine]-1,3-dione

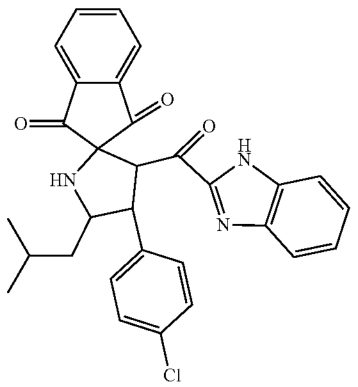 [SMILES: CC(C)CC1NC2(C(=O)c3ccccc3C2=O)C(C(=O)c2nc3ccccc3[nH]2)C1c1ccc(Cl)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 422 mg (3 mmol) of p-chlorobenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 751 mg of a product: (E)-1-(1H-benzo[d]imidazol-2-yl)-3-(4-chlorophenyl)prop-2-en-1-one. 5 mL of absolute ethanol was added to a reaction flask, then 73 mg (0.56 mmol) of leucine, 158 mg (0.56 mmol) of the (E)-1-(1H-benzo[d]imidazol-2-yl)-3-(4-chlorophenyl)prop-2-en-1-one, and 119 mg (0.67 mmol) of ninhydrin hydrate were added successively to the reaction flask, and a reaction was allowed for 2.5 h at 80° C. under stirring to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 124 mg of a yellow solid, and a melting point of the yellow solid was measured by a micro melting point meter to be 117.3° C. to 120.3° C. $^1H$ NMR (400 MHz, DMSO-$d_6$): δ 13.24 (s, 1H), 8.20-8.17 (m, 1H), 8.00 (td, J=7.5, 1.1 Hz, 1H), 7.74 (td, J=7.4, 1.0 Hz, 1H), 7.51 (d, J=8.6 Hz, 2H), 7.47-7.43 (m, 3H), 7.39-7.36 (m, 1H), 7.25-7.16 (m, 2H), 7.06-6.96 (m, 2H), 6.73 (d, J=8.2 Hz, 1H), 4.49 (d, J=10.1 Hz, 1H), 3.51 (t, J=10.0 Hz, 2H), 1.61-1.49 (m, 2H), 1.47-1.37 (m, 2H), 1.24 (d, J=10.3 Hz, 1H), 1.18 (t, J=7.1 Hz, 1H), 0.75 (d, J=6.6 Hz, 3H), 0.71 (d, J=6.5 Hz, 3H).

Compound 12: 3-(1H-benzimidazol-2-carbonyl)-5-isobutyl-4-p-tolylspiro[inden-2,2'-pyrrolidine]-1,3-dione

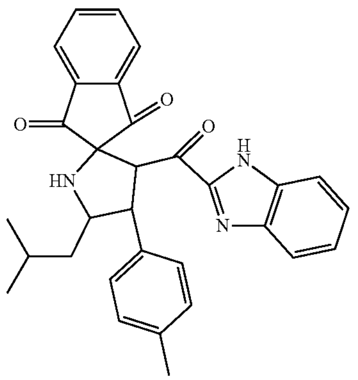 [SMILES: Cc1ccc(C2C(CC(C)C)NC3(C(=O)c4ccccc4C3=O)C2C(=O)c2nc3ccccc3[nH]2)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 360 mg (3 mmol) of p-methylbenzaldehyde was added to the flask to allow a reaction for 10 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 684 mg of a product: 1-(1H-benzimidazol-2-yl)-3-p-tolylprop-2-en-1-one. 147 mg (0.56 mmol) of the 1-(1H-benzimidazol-2-yl)-3-p-tolylprop-2-en-1-one, 119 mg (0.67 mmol) of ninhydrin hydrate, and 73 mg (0.56 mmol) of leucine were weighed, separately; 5 mL of absolute ethanol was first added to a reaction flask, then the weighed leucine, 1-(1H-benzimidazol-2-yl)-3-p-tolylprop-2-en-1-one, and ninhydrin hydrate were added successively to the reaction flask, and a reaction was allowed under reflux at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 97 mg of a solid product, and a melting point of the solid product was measured by a micro melting point meter to be 114.8° C. to 118.1° C. $^1$H NMR (400 MHz, DMSO-$d_6$): δ 13.21 (s, 1H), 8.17 (dd, J=7.7, 1.0 Hz, 1H), 7.98 (td, J=7.5, 1.1 Hz, 2H), 7.73 (td, J=7.5, 1.1 Hz, 1H), 7.45 (dd, J=7.6, 1.0 Hz, 1H), 7.38-7.35 (m, 3H), 7.21-7.16 (m, 3H), 7.05-6.96 (m, 1H), 6.77-6.74 (m, 1H), 4.50 (d, J=10.3 Hz, 1H), 3.46 (t, J=10.3 Hz, 2H), 2.27 (s, 3H), 2.00 (d, J=6.4 Hz, 1H), 1.25 (d, J=10.0 Hz, 1H), 1.20-1.09 (m, 2H), 0.75 (d, J=6.6 Hz, 3H), 0.70 (d, J=6.6 Hz, 3H).

Compound 13: 3-(1H-benzimidazol-2-carbonyl)-4, 4-diethoxyphenyl-5-isobutylspiro[inden-2,2'-pyrrolidine]-1,3-dione

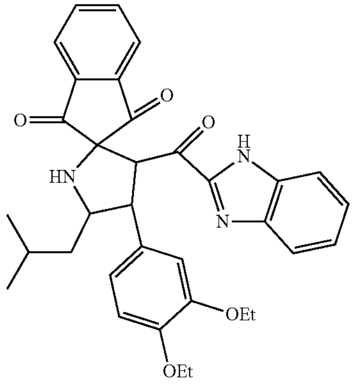 [SMILES: CCOc1ccc(C2C(CC(C)C)NC3(C(=O)c4ccccc4C3=O)C2C(=O)c2nc3ccccc3[nH]2)cc1OCC]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 582 mg (3 mmol) of 3,4-diethoxybenzaldehyde was added to the flask to allow a reaction for 8 h to obtain a reaction solution;

monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 890 mg of a product: 1-(1H-benzimidazol-2-yl)-3-(3,4-diethoxyphenyl) prop-2-en-1-one. 5 mL of absolute ethanol was added to a reaction flask, then 73 mg (0.56 mmol) of leucine, 188 mg (0.56 mmol) of the 1-(1H-benzimidazol-2-yl)-3-(3,4-diethoxyphenyl)prop-2-en-1-one, and 119 mg (0.67 mmol) of ninhydrin hydrate were added successively to the reaction flask, and a reaction was allowed at 80° C. for 8 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 65 mg of a yellow solid, and a melting point of the yellow solid was measured by a micro melting point meter to be 68.9° C. to 71.5° C. $^{1}H$ NMR (400 MHz, DMSO-$d_6$): δ 13.22 (s, 1H), 8.16 (dd, J=7.7, 1.0 Hz, 1H), 7.99 (td, J=7.5, 1.1 Hz, 1H), 7.74 (td, J=7.5, 1.1 Hz, 1H), 7.48-7.44 (m, 1H), 7.39-7.35 (m, 1H), 7.25-7.16 (m, 1H), 7.07 (d, J=1.8 Hz, 1H), 7.06-6.97 (m, 2H), 6.97-6.95 (m, 1H), 6.92 (d, J=8.3 Hz, 1H), 6.76 (d, J=8.3 Hz, 1H), 4.48 (d, J=10.2 Hz, 1H), 4.08 (dd, J=7.0, 5.3 Hz, 2H), 3.98 (q, J=7.0 Hz, 2H), 3.44 (t, J=10.2 Hz, 1H), 1.35 (t, J=6.9 Hz, 4H), 1.30 (d, J=2.0 Hz, 3H), 1.26 (s, 1H), 1.23 (s, 2H), 0.76 (d, J=6.6 Hz, 3H), 0.72 (d, J=6.5 Hz, 3H).

Compound 14: 3-(1H-benzimidazol-2-carbonyl)-4-(3-bromophenyl)-5-isobutylspiro[inden-2,2'-pyrrolidine]-1,3-dione

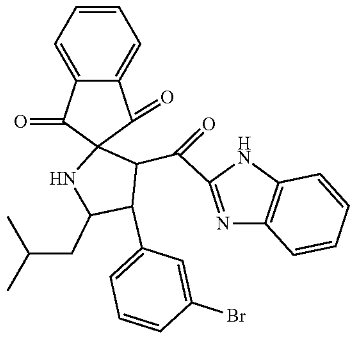 [SMILES: CC(C)CC1NC2(C(=O)c3ccccc3C2=O)C(C(=O)c2nc3ccccc3[nH]2)C1c1cccc(Br)c1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 3-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-3-bromophenylprop-2-en-1-one. 5 mL of absolute ethanol was added to a reaction flask, then 73 mg (0.56 mmol) of leucine, 183 mg (0.56 mmol) of the 1-benzimidazol-2-yl-3-bromophenylprop-2-en-1-one, and 119 mg (0.67 mmol) of ninhydrin hydrate were added successively to the reaction flask, and a reaction was allowed at 80° C. for 8 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 65 mg of a yellow solid, and a melting point of the yellow solid was measured by a micro melting point meter to be 145.7° C. to 147.8° C. $^{1}H$ NMR (500 MHz, Chloroform-d): δ 8.01 (dd, J=5.6, 3.9 Hz, 3H), 7.90-7.82 (m, 4H), 7.54 (s, 1H), 7.53-7.37 (m, 5H), 7.28 (s, 1H), 7.06 (s, 1H), 7.04-6.98 (m, 2H), 4.41 (t, J=0.9 Hz, 1H), 3.86 (s, 1H), 3.58 (s, 1H), 1.79 (d, J=2.9 Hz, 3H), 1.70 (s, 1H), 0.92 (s, 3H), 0.88 (s, 3H).

Compound 15: 3-(1H-benzimidazol-2-carbonyl)-4-(4-ethoxyphenyl)-5-isobutylspiro[inden-2,2'-pyrrolidine]-1,3-dione

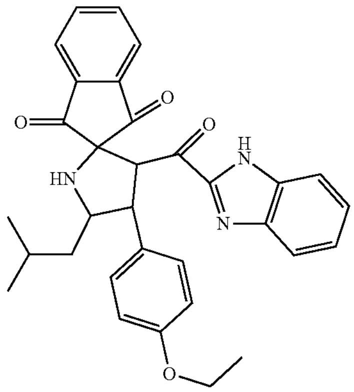 [SMILES: CCOc1ccc(C2C(CC(C)C)NC3(C(=O)c4ccccc4C3=O)C2C(=O)c2nc3ccccc3[nH]2)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 450 mg (3 mmol) of 4-ethoxybenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 890 mg of a product: 1-benzimidazol-2-yl-3-(4-ethoxyphenyl)prop-2-en-1-one. 5 mL of absolute ethanol was added to a reaction flask, then 73 mg (0.56 mmol) of leucine, 163 mg (0.56 mmol) of the 1-benzimidazol-2-yl-3-(4-ethoxyphenyl)prop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 114 mg of the final product: 2-(1H-benzimidazol-2-carbonyl)-1-(4-ethoxyphenyl)-1,2,5,6,7,7a-hexahydrospiroinden-2,3-pyrrolizine-1,3-dione, and a melting point of the final product was measured by a micro melting point meter to be 145.3° C. to 148.7° C. $^1H$ NMR (500 MHz, Chloroform-d): δ 8.01 (dd, J=5.6, 3.9 Hz, 3H), 7.92-7.82 (m, 4H), 7.56 (d, J=7.5 Hz, 3H), 7.37 (s, 1H), 7.27 (s, 1H), 7.12-7.06 (m, 3H), 6.96-6.90 (m, 3H), 4.48 (t, J=1.0 Hz, 1H), 3.97 (s, 2H), 3.86 (s, 1H), 3.58 (s, 1H), 1.89 (d, J=12.3 Hz, 1H), 1.83 (d, J=12.5 Hz, 1H), 1.70 (s, 1H), 1.41 (s, 3H), 0.93 (s, 3H), 0.88 (s, 3H).

Compound 16: 3-(1H-benzimidazol-2-carbonyl)-4-(4-bromophenyl)-5-isobutylspiro[inden-2,2'-pyrrolidine]-1,3-dione

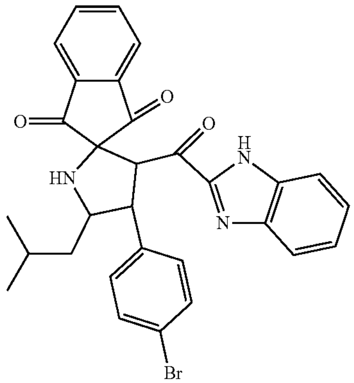 [SMILES: CC(C)CC1NC2(C(=O)c3ccccc3C2=O)C(C(=O)c2nc3ccccc3[nH]2)C1c1ccc(Br)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 4-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-4-bromophenylprop-2-en-1-one. 5 mL of absolute ethanol was added to a reaction flask, then 73 mg (0.56 mmol) of leucine, 183 mg (0.56 mmol) of the 1-benzimidazol-2-yl-4-bromophenylprop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 124 mg of the final product: 3-(1H-benzimidazol-2-carbonyl)-4-(4-bromophenyl)-5-isobutylspiro[inden-2,2'-pyrrolidine]-1,3-dione, and a melting point of the final product was measured by a micro melting point meter to be 241.2° C. to 243.6° C. $^1$H NMR (500 MHz, Chloroform-d): δ 8.05 (dd, J=5.7, 3.8 Hz, 3H), 7.90-7.82 (m, 4H), 7.59-7.51 (m, 5H), 7.39 (s, 1H), 7.28 (s, 1H), 7.18-7.12 (m, 3H), 4.41 (t, J=0.9 Hz, 1H), 3.86 (s, 1H), 3.58 (s, 1H), 1.79 (d, J=2.9 Hz, 3H), 1.70 (s, 1H), 0.92 (s, 3H), 0.88 (s, 3H).

Compound 17: 3-(1H-benzimidazol-2-carbonyl)-5-sec-butyl-4-cyclohexylspiro[inden-2,2'-pyrrolidine]-1,3-dione

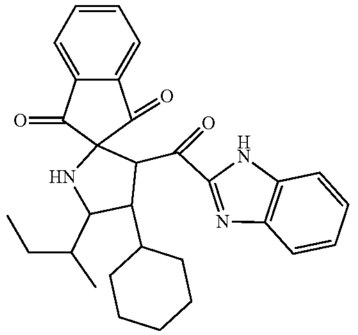 [SMILES: CCC(C)C1NC2(C(=O)c3ccccc3C2=O)C(C(=O)c2nc3ccccc3[nH]2)C1C1CCCCC1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 336 mg (3 mmol) of cyclohexanecarboxaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 580 mg of a product: 1-(1H-benzimidazol-2-yl)-3-cyclohexylprop-2-en-1-one. 142 mg (0.56 mmol) of the 1-(1H-benzimidazol-2-yl)-3-cyclohexylprop-2-en-1-one, 119 mg (0.67 mmol) of ninhydrin hydrate, and 73 mg (0.56 mmol) of isoleucine were weighed, separately; 3 mL of absolute ethanol was first added to a reaction flask, then the weighed isoleucine, 1-(1H-benzimidazol-2-yl)-3-cyclohexylprop-2-en-1-one, and ninhydrin hydrate were added successively to the reaction flask, and a reaction was allowed under reflux at 80° C. for 3.5 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 91 mg of a solid, and a melting point of the solid was measured by a micro melting point meter to be 97.8° C. to 100.8° C. $^1$H NMR (400 MHz, DMSO-$d_6$): δ 13.21 (d, J=4.3 Hz, 1H), 8.09-8.01 (m, 1H), 7.95-7.89 (m, 1H), 7.72-7.63 (m, 1H), 7.43-7.34 (m, 2H), 7.28-7.19 (m, 1H), 7.09-7.00 (m, 1H), 6.89 (d, J=8.2 Hz, 1H), 4.30-4.26 (m, 1H), 3.51 (s, 1H), 2.81-2.68 (m, 1H), 1.82-1.55 (m, 8H), 1.42-1.28 (m, 2H), 1.27-1.18 (m, 4H), 0.94 (d, J=6.7 Hz, 1H), 0.89 (dd, J=8.5, 7.0 Hz, 6H).

Compound 18: 3-(1H-benzimidazol-2-carbonyl)-5-sec-butyl-4-(3-fluoro-4-chlorophenyl)spiro[inden-2,2'-pyrrolidine]-1,3-dione

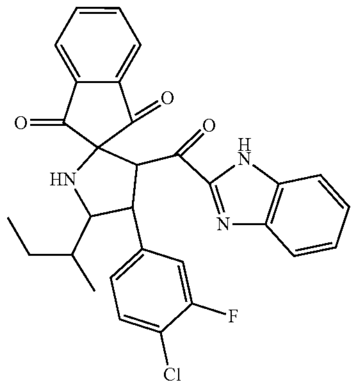 [SMILES: CCC(C)C1NC2(C(=O)c3ccccc3C2=O)C(C(=O)c2nc3ccccc3[nH]2)C1c1ccc(Cl)c(F)c1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 475 mg (3 mmol) of 3-fluoro-4-chlorobenzaldehyde was added to the flask to allow a reaction for 10 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 823 mg of a product: (E)-1-(1H-benzo[d]imidazol-2-yl)-3-(3-fluoro-4-chlorophenyl)prop-2-en-1-one. 5 mL of absolute ethanol was added to a reaction flask, then 73 mg (0.56 mmol) of isoleucine, 168 mg (0.56 mmol) of the (E)-1-(1H-benzo[d]imidazol-2-yl)-3-(3-fluoro-4-chlorophenyl)prop-2-en-1-one, and 119 mg (0.67 mmol) of ninhydrin hydrate were added successively to the reaction flask, and a reaction was allowed for 2 h at 80° C. to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 101 mg of a yellow solid, and a melting point of the yellow solid was measured by a micro melting point meter to be 104.1° C. to 108.3° C. $^1$H NMR (400 MHz, DMSO-$d_6$): δ 13.22 (s, 1H), 8.17 (dd, J=7.5, 2.7 Hz, 1H), 7.98 (td, J=7.5, 1.1 Hz, 1H), 7.75 (tt, J=7.5, 1.2 Hz, 1H), 7.62-7.57 (m, 1H), 7.57-7.49 (m, 2H), 7.47 (dd, J=7.7, 1.1 Hz, 1H), 7.42-7.34 (m, 3H), 7.26-7.17 (m, 1H), 7.06-6.97 (m, 1H), 6.74 (d, J=8.3 Hz, 1H), 4.44 (dd, J=12.6, 10.1 Hz, 1H), 3.82 (t, J=10.1 Hz, 1H), 3.67 (d, J=10.0 Hz, 1H), 3.39 (s, 1H), 1.40-1.30 (m, 2H), 1.24 (d, J=11.5 Hz, 1H), 0.86 (d, J=6.5 Hz, 3H), 0.77-0.74 (m, 3H).

Compound 19: 3-(1H-benzimidazol-2-carbonyl)-5-sec-butyl-4-(4-chlorophenyl)spiro[inden-2,2'-pyrrolidine]-1,3-dione

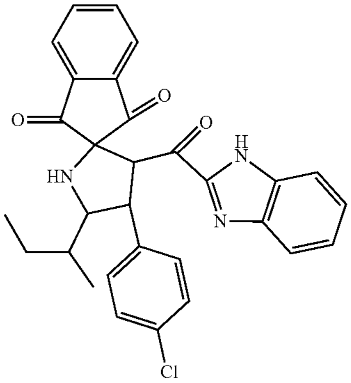 [SMILES: CCC(C)C1NC2(C(=O)c3ccccc3C2=O)C(C(=O)c2nc3ccccc3[nH]2)C1c1ccc(Cl)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 422 mg (3 mmol) of p-chlorobenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 751 mg of a product: (E)-1-(1H-benzo[d]imidazol-2-yl)-3-(4-chlorophenyl)prop-2-en-1-one. 5 mL of absolute ethanol was added to a reaction flask, then 73 mg (0.56 mmol) of isoleucine, 158 mg (0.56 mmol) of the (E)-1-(1H-benzo[d]imidazol-2-yl)-3-(4-chlorophenyl)prop-2-en-1-one, and 119 mg (0.67 mmol) of ninhydrin hydrate were added successively to the reaction flask, and a reaction was allowed for 2.5 h at 80° C. under stirring to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 203 mg of a yellow solid, and a melting point of the yellow solid was measured by a micro melting point meter to be 98.5° C. to 100.5° C. $^1H$ NMR (400 MHz, DMSO-$d_6$): δ 13.20 (s, 1H), 8.20-8.12 (m, 1H), 7.97 (td, J=7.5, 1.1 Hz, 1H), 7.73 (td, J=7.5, 1.1 Hz, 1H), 7.53 (d, J=4.0 Hz, 1H), 7.52 (d, J=2.1 Hz, 1H), 7.48-7.42 (m, 3H), 7.38-7.35 (m, 1H), 7.25-7.16 (m, 2H), 7.06-6.97 (m, 1H), 6.76 (d, J=8.3 Hz, 1H), 4.50-4.39 (m, 1H), 3.79 (t, J=10.3 Hz, 1H), 3.68 (dd, J=10.6, 3.7 Hz, 1H), 3.37 (d, J=1.9 Hz, 1H), 2.03 (d, J=27.9 Hz, 1H), 1.35-1.32 (m, 1H), 1.30 (s, 1H), 1.25 (d, J=10.2 Hz, 3H), 0.85 (d, J=6.6 Hz, 3H).

Compound 20: 3-(1H-benzimidazol-2-carbonyl)-5-sec-butyl-4-p-tolylspiro[inden-2,2'-pyrrolidine]-1,3-dione

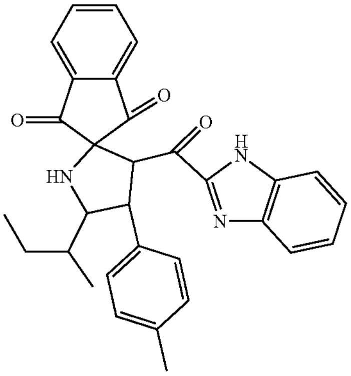 [SMILES: CCC(C)C1NC2(C(=O)c3ccccc3C2=O)C(C(=O)c2nc3ccccc3[nH]2)C1c1ccc(C)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 360 mg (3 mmol) of p-methylbenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 684 mg of a product: 1-(1H-benzimidazol-2-yl)-3-p-tolylprop-2-en-1-one. 147 mg (0.56 mmol) of the 1-(1H-benzimidazol-2-yl)-3-p-tolylprop-2-en-1-one, 119 mg (0.67 mmol) of ninhydrin hydrate, and 73 mg (0.56 mmol) of isoleucine were weighed, separately; 5 mL of absolute ethanol was first added to a reaction flask, then the weighed isoleucine, 1-(1H-benzimidazol-2-yl)-3-p-tolylprop-2-en-1-one, and ninhydrin hydrate were added successively to the reaction flask, and a reaction was allowed under reflux at 80° C. for 2 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 102 mg of a solid, and a melting point of the solid was measured by a micro melting point meter to be 103.0° C. to 107.8° C. $^1H$ NMR (400 MHz, DMSO-$d_6$): δ 13.18 (s, 1H), 8.14 (dd, J=7.6, 2.8 Hz, 1H), 7.99-7.92 (m, 1H), 7.75-7.67 (m, 1H), 7.45 (d, J=7.6 Hz, 1H), 7.41-7.33 (m, 3H), 7.23-7.13 (m, 3H), 7.04-6.98 (m, 1H), 6.79 (d, J=8.3 Hz, 1H), 4.47 (t, J=10.4 Hz, 1H), 3.81-3.72 (m, 1H), 3.68 (d, J=10.1 Hz, 1H), 3.44 (s, 1H), 2.26 (s, 3H), 1.30 (q, J=3.6, 3.1 Hz, 1H), 1.28-1.15 (m, 2H), 0.85 (d, J=6.7 Hz, 2H), 0.79-0.68 (m, 4H).

Compound 21: 3-(1H-benzimidazol-2-carbonyl)-4, 4-diethoxyphenyl-5-isobutylspiro[inden-2,2'-pyrrolidine]-1,3-dione

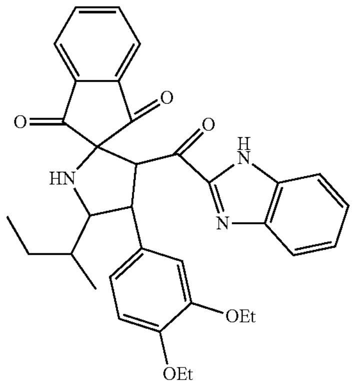 [SMILES: CCOc1ccc(C2C(C(C)CC)NC3(C(=O)c4ccccc4C3=O)C2C(=O)c2nc3ccccc3[nH]2)cc1OCC]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 582 mg (3 mmol) of 3,4-diethoxybenzaldehyde was added to the flask to allow a reaction for 8 h to obtain a reaction solution; monitoring analysis was conducted by TLC, and when a monitoring analysis result showed that the reaction was completed, the reaction solution was poured into a beaker;

an appropriate amount of distilled water was added to the beaker, and the beaker was allowed to stand to make a yellow solid precipitated; and the yellow solid was collected through suction filtration and dried to obtain 890 mg of a product: 1-(1H-benzimidazol-2-yl)-3-(3,4-diethoxyphenyl) prop-2-en-1-one. 5 mL of absolute ethanol was added to a reaction flask, then 73 mg (0.56 mmol) of isoleucine, 188 mg (0.56 mmol) of the 1-(1H-benzimidazol-2-yl)-3-(3,4-diethoxyphenyl)prop-2-en-1-one, and 119 mg (0.67 mmol) of ninhydrin hydrate were added successively to the reaction flask, and a reaction was allowed at room temperature for 8 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 159 mg of a yellow solid, and a melting point of the yellow solid was measured by a micro melting point meter to be 95.5° C. to 98.5° C. $^1$H NMR (400 MHz, DMSO-$d_6$): δ 13.20 (s, 1H), 8.16-8.11 (m, 1H), 7.96 (td, J=7.5, 1.0 Hz, 1H), 7.73 (td, J=7.4, 1.1 Hz, 1H), 7.46 (d, J=7.7 Hz, 1H), 7.36 (d, J=8.1 Hz, 1H), 7.21 (t, J=7.6 Hz, 1H), 7.09 (dd, J=5.6, 2.0 Hz, 1H), 7.05-6.95 (m, 2H), 6.95-6.87 (m, 1H), 6.79 (d, J=8.3 Hz, 1H), 4.45 (dd, J=9.7, 6.7 Hz, 1H), 4.08 (qd, J=7.0, 2.0 Hz, 2H), 3.97 (qd, J=7.0, 2.6 Hz, 2H), 3.79-3.62 (m, 2H), 1.35 (td, J=6.9, 1.1 Hz, 4H), 1.31-1.25 (m, 4H), 1.23 (s, 1H), 0.86 (d, J=6.5 Hz, 2H), 0.80-0.71 (m, 4H).

Compound 22: 3-benzimidazol-2-carbonyl-4-(3-bromophenyl)-5-sec-butylspiro[inden-2,2'-pyrrolidine]-1,3-dione

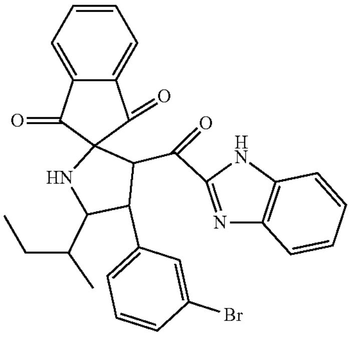 [SMILES: CCC(C)C1NC2(C(=O)c3ccccc3C2=O)C(C(=O)c2nc3ccccc3[nH]2)C1c1cccc(Br)c1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 3-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-3-bromophenylprop-2-en-1-one. 5 mL of absolute ethanol was added to a reaction flask, then 73 mg (0.56 mmol) of isoleucine, 183 mg (0.56 mmol) of the 1-benzimidazol-2-yl-3-bromophenylprop-2-en-1-one, and 119 mg (0.67 mmol) of ninhydrin hydrate were added successively to the reaction flask, and a reaction was allowed at 80° C. for 8 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 75 mg of a yellow solid, and a melting point of the yellow solid was measured by a micro melting point meter to be 204.4° C. to 206.9° C. $^1$H NMR (500 MHz, Chloroform-d): δ 8.01 (dd, J=5.6, 3.9 Hz, 3H), 7.90-7.82 (m, 4H), 7.56-7.46 (m, 4H), 7.39 (s, 1H), 7.33-7.26 (m, 3H), 7.04-6.98 (m, 2H), 6.02 (s, 1H), 4.41 (t, J=1.0 Hz, 1H), 3.86 (s, 1H), 3.76 (s, 1H), 2.04 (s, 1H), 1.76 (d, J=12.5 Hz, 1H), 1.26 (d, J=12.5 Hz, 1H), 0.93 (s, 3H), 0.87 (s, 3H).

Compound 23: 3-(1H-benzimidazol-2-carbonyl)-5-sec-butyl-4-(4-ethoxyphenyl)spiro[inden-2,2'-pyrrolidine]-1,3-dione

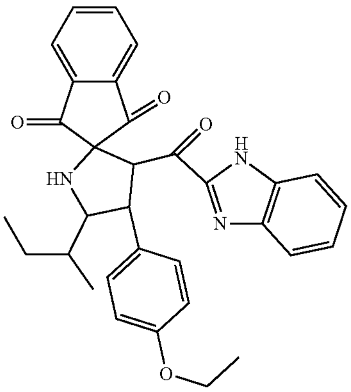 [SMILES: CCOc1ccc(C2C(C(C)CC)NC3(C(=O)c4ccccc4C3=O)C2C(=O)c2nc3ccccc3[nH]2)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 450 mg (3 mmol) of 4-ethoxybenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 890 mg of a product: 1-benzimidazol-2-yl-3-(4-ethoxyphenyl)prop-2-en-1-one. 5 mL of absolute ethanol was added to a reaction flask, then 73 mg (0.56 mmol) of isoleucine, 163 mg (0.56 mmol) of the 1-benzimidazol-2-yl-3-(4-ethoxyphenyl)prop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 104 mg of the final product: 3-(1H-benzimidazol-2-carbonyl)-5-sec-butyl-4-(4-ethoxyphenyl)spiro[inden-2,2'-pyrrolidine]-1,3-dione, and a melting point of the final product was measured by a micro melting point meter to be 178.3° C. to 180.1° C. $^1H$ NMR (500 MHz, Chloroform-d): δ 8.01 (dd, J=5.6, 3.9 Hz, 3H), 7.92-7.82 (m, 4H), 7.56 (s, 1H), 7.37 (s, 1H), 7.27 (s, 1H), 7.12-7.06 (m, 3H), 6.95-6.89 (m, 3H), 6.50 (s, 1H), 4.51 (t, J=1.0 Hz, 1H), 3.97 (s, 2H), 3.86 (s, 1H), 3.80 (s, 1H), 2.04 (s, 1H), 1.71 (d, J=12.4 Hz, 1H), 1.41 (s, 3H), 1.21 (d, J=12.5 Hz, 1H), 0.94 (s, 3H), 0.88 (s, 3H).

Compound 24: 3-(1H-benzimidazol-2-carbonyl)-4-(4-bromophenyl)-5-sec-butylspiro[inden-2,2'-pyrrolidine]-1,3-dione

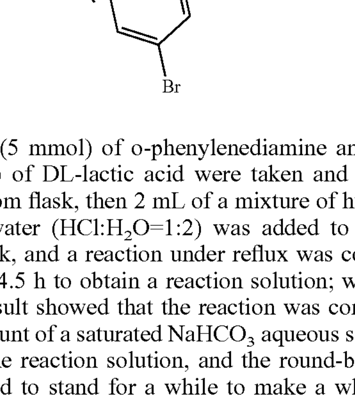

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 4-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-4-bromophenylprop-2-en-1-one. 5 mL of absolute ethanol was added to a reaction flask, then 73 mg (0.56 mmol) of isoleucine, 183 mg (0.56 mmol) of the 1-benzimidazol-2-yl-4-bromophenylprop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 94 mg of the final product: 3-(1H-benzimidazol-2-carbonyl)-4-(4-bromophenyl)-5-sec-butyl-spiro[inden-2,2'-pyrrolidine]-1,3-dione, and a melting point of the final product was measured by a micro melting point meter to be 119.0° C. to 120.9° C. $^1$H NMR (500 MHz, Chloroform-d): δ 8.01 (dd, J=5.6, 3.9 Hz, 3H), 7.90-7.82 (m, 4H), 7.57-7.51 (m, 4H), 7.39 (s, 1H), 7.28 (s, 1H), 7.18-7.12 (m, 3H), 6.50 (s, 1H), 4.41 (t, J=1.0 Hz, 1H), 3.86 (s, 1H), 3.76 (s, 1H), 2.04 (s, 1H), 1.76 (d, J=12.5 Hz, 1H), 1.26 (d, J=12.5 Hz, 1H), 0.93 (s, 3H), 0.88 (s, 3H).

Compound 25: 3-(1H-benzimidazol-2-carbonyl)-4-cyclohexyl-5-isopropylspiro[inden-2,2'-pyrrolidine]-1,3-dione

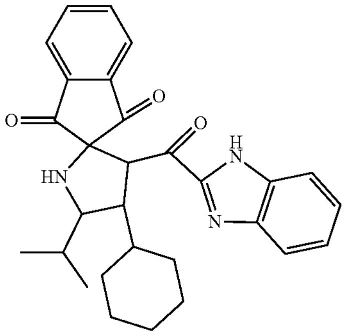 [SMILES: CC(C)C1NC2(C(=O)c3ccccc3C2=O)C(C(=O)c2nc3ccccc3[nH]2)C1C1CCCCC1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 336 mg (3 mmol) of cyclohexanecarboxaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 580 mg of a product: 1-(1H-benzimidazol-2-yl)-3-cyclohexylprop-2-en-1-one. 142 mg (0.56 mmol) of the 1-(1H-benzimidazol-2-yl)-3-cyclohexylprop-2-en-1-one, 119 mg (0.67 mmol) of ninhydrin hydrate, and 65 mg (0.56 mmol) of valine were weighed and added to a reaction flask, 5 mL of absolute ethanol was added to the reaction flask, and a reaction was allowed at 80° C. for 4.5 h to obtain a reaction solution; monitoring analysis was conducted by TLC (PE:EA=3:1), and when a monitoring analysis result showed that the reaction was completed, the reaction solution was concentrated under vacuum to obtain a concentrate; an appropriate amount of a column chromatography silica gel was weighed and prepared into a silica gel sand, and the concentrate was purified by a rapid preparative chromatograph with the silica gel sand to obtain a purified product, where the whole purification process was monitored by TLC; and the purified product was collected and spin-dried to obtain 98 mg of a yellow solid, and a melting point of the yellow solid was measured by a micro melting point meter to be 102.3° C. to 104.0° C. $^1$H NMR (400 MHz, DMSO-$d_6$): δ 13.21 (s, 1H), 8.05 (d, J=7.6 Hz, 1H), 7.90 (t, J=7.5 Hz, 1H), 7.68 (t, J=7.5 Hz, 1H), 7.39 (t, J=7.6 Hz, 2H), 7.23 (t, J=7.6 Hz, 1H), 7.04 (t, J=7.7 Hz, 1H), 6.89 (d, J=8.2 Hz, 1H), 4.28 (d, J=8.0 Hz, 1H), 3.12 (s, 1H), 2.77 (td, J=8.1, 5.1 Hz, 1H), 1.82-1.55 (m, 7H), 1.28-1.03 (m, 6H), 0.95 (d, J=6.9 Hz, 3H), 0.90 (d, J=6.7 Hz, 3H).

Compound 26: 3-(1H-benzimidazol-2-carbonyl)-4-(3-fluoro-4-chlorophenyl)-5-isopropylspiro[inden-2,2'-pyrrolidine]-1,3-dione

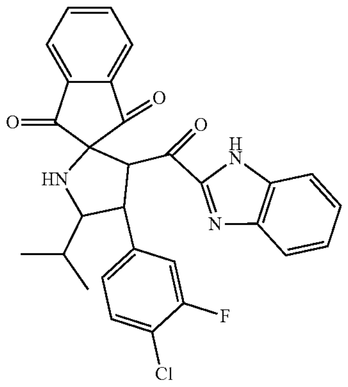 [SMILES: CC(C)C1NC2(C(=O)c3ccccc3C2=O)C(C(=O)c2nc3ccccc3[nH]2)C1c1ccc(Cl)c(F)c1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 475 mg (3 mmol) of 3-fluoro-4-chlorobenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 812 mg of a product: (E)-1-(1H-benzo[d]imidazol-2-yl)-3-(3-fluoro-4-chlorophenyl)prop-2-en-1-one. 168 mg (0.56 mmol) of the (E)-1-(1H-benzo[d]imidazol-2-yl)-3-(3-fluoro-4-chlorophenyl)prop-2-en-1-one, 119 mg (0.67 mmol) of ninhydrin hydrate, and 65 mg (0.56 mmol) of valine were weighed, separately; 4 mL of absolute ethanol was first added to a reaction flask, then the weighed valine, (E)-1-(1H-benzo[d]imidazol-2-yl)-3-(3-fluoro-4-chlorophenyl)prop-2-en-1-one, and ninhydrin hydrate were added successively to the reaction flask, and a reaction was allowed under reflux at 80° C. for 2.5 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 103 mg of a solid, and a melting point of the solid was measured by a micro melting point meter to be 114.0° C. to 117.5° C. $^1$H NMR (400 MHz, DMSO-$d_6$): δ 13.23 (s, 1H), 8.17 (d, J=7.6 Hz, 1H), 7.9 (t, J=7.5 Hz, 1H), 7.75 (t, J=7.5 Hz, 1H), 7.58 (t, J=8.1 Hz, 1H), 7.56-7.52 (m, 1H), 7.48 (d, J=7.6 Hz, 1H), 7.41-7.3 (m, 2H), 7.21 (t, J=7.6 Hz, 1H), 7.02 (t, J=7.7 Hz, 1H), 6.75 (d, J=8.3 Hz, 1H), 4.45 (d, J=10.1 Hz, 1H), 3.80 (t, J=10.1 Hz, 1H), 3.60-3.51 (m, 1H), 1.75-1.65 (m, 1H), 1.28-1.20 (m, 1H), 0.85 (d, J=6.7 Hz, 3H), 0.76 (d, J=6.8 Hz, 3H).

Compound 27: 3-(1H-benzimidazol-2-carbonyl)-4-(4-chlorophenyl)-5-isopropylspiro[inden-2,2'-pyrrolidine]-1,3-dione

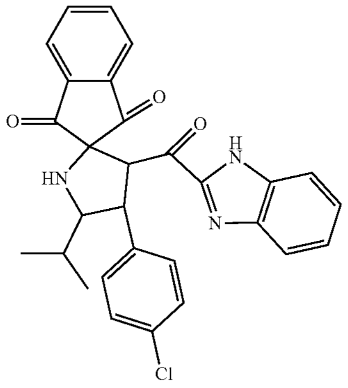 [SMILES: CC(C)C1NC2(C(=O)c3ccccc3C2=O)C(C(=O)c2nc3ccccc3[nH]2)C1c1ccc(Cl)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 422 mg (3 mmol) of p-chlorobenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 751 mg of a product: (E)-1-(1H-benzo[d]imidazol-2-yl)-3-(4-chlorophenyl)prop-2-en-1-one. 5 mL of absolute ethanol was added to a reaction flask, then 65 mg (0.56 mmol) of valine, 158 mg (0.56 mmol) of the (E)-1-(1H-benzo[d]imidazol-2-yl)-3-(4-chlorophenyl)prop-2-en-1-one, and 119 mg (0.67 mmol) of ninhydrin hydrate were added successively to the reaction flask, and a reaction was allowed for 2 h at 80° C. under stirring to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and concentrated under vacuum to obtain 53 mg of a yellow solid, and a melting point of the yellow solid was measured by a micro melting point meter to be 103.3° C. to 105.4° C. $^1H$ NMR (400 MHz, DMSO-$d_6$): δ 13.21 (s, 1H), 8.15 (d, J=7.6 Hz, 1H), 8.01-7.92 (m, 1H), 7.76-7.70 (m, 1H), 7.55 (s, 1H), 7.53 (s, 1H), 7.50-7.38 (m, 3H), 7.40-7.33 (m, 1H), 7.25-7.16 (m, 1H), 7.06-6.97 (m, 1H), 6.76 (d, J=8.2 Hz, 1H), 4.45 (d, J=10.2 Hz, 1H), 3.77 (t, J=10.3 Hz, 1H), 3.61-3.51 (m, 1H), 1.72-1.59 (m, 1H), 1.32 (d, J=15.1 Hz, 1H), 0.83 (d, J=6.7 Hz, 3H), 0.74 (d, J=6.9 Hz, 3H).

Compound 28: 3-(1H-benzimidazol-2-carbonyl)-5-isopropyl-4-p-tolylspiro[inden-2,2'-pyrrolidine]-1,3-dione

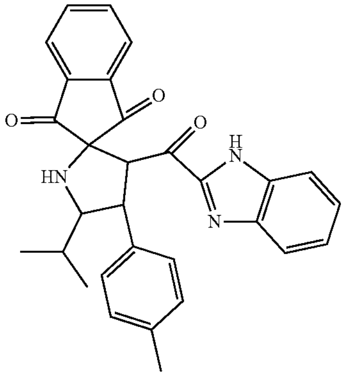 [SMILES: Cc1ccc(C2C(C(C)C)NC3(C(=O)c4ccccc4C3=O)C2C(=O)c2nc3ccccc3[nH]2)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 360 mg (3 mmol) of p-methylbenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 684 mg of a product: 1-(1H-benzimidazol-2-yl)-3-p-tolylprop-2-en-1-one. 147 mg (0.56 mmol) of the 1-(1H-benzimidazol-2-yl)-3-p-tolylprop-2-en-1-one, 119 mg (0.67 mmol) of ninhydrin hydrate, and 65 mg (0.56 mmol) of valine were weighed, separately; 5 mL of absolute ethanol was first added to a reaction flask, then the weighed valine, 1-(1H-benzimidazol-2-yl)-3-p-tolylprop-2-en-1-one, and ninhydrin hydrate were added successively to the reaction flask, and a reaction was allowed under reflux at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 147 mg of a solid, and a melting point of the solid was measured by a micro melting point meter to be 114.1° C. to 116.3° C. $^{1}$H NMR (400 MHz, DMSO-d6): δ 13.18 (s, 1H), 8.13 (d, J=7.6 Hz, 1H), 7.95 (t, J=7.5 Hz, 1H), 7.72 (t, J=7.5 Hz, 1H), 7.45 (d, J=7.6 Hz, 1H), 7.42-7.32 (m, 3H), 7.21 (d, J=7.2 Hz, 1H), 7.16 (d, J=7.9 Hz, 2H), 7.01 (t, J=7.6 Hz, 1H), 6.79 (d, J=8.2 Hz, 1H), 4.47 (d, J=10.2 Hz, 1H), 3.76-3.69 (m, 1H), 3.56 (d, J=5.8 Hz, 1H), 2.25 (s, 3H), 1.69-1.60 (m, 1H), 1.25 (d, J=9.6 Hz, 1H), 0.84 (d, J=6.7 Hz, 3H), 0.74 (d, J=6.9 Hz, 3H).

Compound 29: 3-(1H-benzimidazol-2-carbonyl)-3,4-diethoxyphenyl-5-isopropylspiro[inden-2,2'-pyrrolidine]-1,3-dione

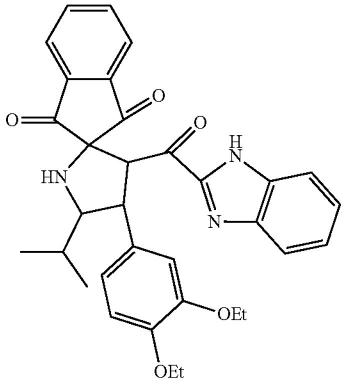 [SMILES: CCOc1ccc(C2C(C(C)C)NC3(C(=O)c4ccccc4C3=O)C2C(=O)c2nc3ccccc3[nH]2)cc1OCC]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 582 mg (3 mmol) of 3,4-diethoxybenzaldehyde was added to the flask to allow a reaction for 8 h to obtain a reaction solution;

monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 890 mg of a product: 1-(1H-benzimidazol-2-yl)-3-(3,4-diethoxyphenyl) prop-2-en-1-one. 5 mL of absolute ethanol was added to a reaction flask, then 65 mg (0.56 mmol) of valine, 188 mg (0.56 mmol) of the 1-(1H-benzimidazol-2-yl)-3-(3,4-diethoxyphenyl)prop-2-en-1-one, and 119 mg (0.67 mmol) of ninhydrin hydrate were added successively to the reaction flask, and a reaction was allowed at 80° C. for 3.5 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 95 mg of the final product: 3-(1H-benzimidazol-2-carbonyl)-3,4-diethoxyphenyl-5-isopropylspiro[inden-2,2'-pyrrolidine]-1,3-dione, and a melting point of the final product was measured by a micro melting point meter to be 96.5° C. to 98.5° C. $^1$H NMR (400 MHz, DMSO-$d_6$): δ 13.20 (s, 1H), 8.17-8.09 (m, 1H), 7.96 (td, J=7.5, 1.1 Hz, 1H), 7.73 (td, J=7.5, 1.1 Hz, 1H), 7.46 (dt, J=7.7, 1.0 Hz, 1H), 7.41-7.33 (m, 1H), 7.25-7.16 (m, 1H), 7.10 (d, J=2.0 Hz, 1H), 7.07-6.99 (m, 2H), 7.03-6.94 (m, 2H), 6.91 (d, J=8.3 Hz, 1H), 6.80 (d, J=8.2 Hz, 1H), 4.46 (d, J=10.1 Hz, 1H), 4.09 (d, J=7.0 Hz, 3H), 3.97 (q, J=7.0 Hz, 3H), 3.71 (t, J=10.1 Hz, 1H), 3.55 (dd, J=10.6, 5.0 Hz, 2H), 1.74-1.61 (m, 1H), 1.35 (t, J=7.0 Hz, 4H), 1.29 (t, J=7.0 Hz, 5H), 1.18 (t, J=7.1 Hz, 2H), 0.85 (d, J=6.8 Hz, 4H), 0.77 (d, J=6.9 Hz, 4H).

Compound 30: 3-(1H-benzimidazol-2-carbonyl)-4-(3-bromophenyl)-5-isopropylspiro[inden-2,2'-pyrrolidine]-1,3-dione

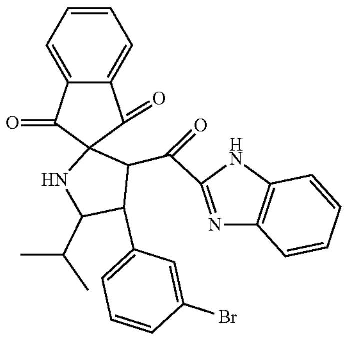 [SMILES: CC(C)C1NC2(C(=O)c3ccccc3C2=O)C(C(=O)c2nc3ccccc3[nH]2)C1c1cccc(Br)c1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 3-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-3-bromophenylprop-2-en-1-one. 5 mL of absolute ethanol was added to a reaction flask, then 65 mg (0.56 mmol) of valine, 183 mg (0.56 mmol) of the 1-benzimidazol-2-yl-3-bromophenylprop-2-en-1-one, and 119 mg (0.67 mmol) of ninhydrin hydrate were added successively to the reaction flask, and a reaction was allowed at 80° C. for 8 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 68 mg of a yellow solid, and a melting point of the yellow solid was measured by a micro melting point meter to be 189.5° C. to 191.5° C. $^1$H NMR (500 MHz, Chloroform-d): δ 8.07 (dd, J=5.7, 3.8 Hz, 2H), 7.90-7.82 (m, 3H), 7.55 (s, 1H), 7.53-7.45 (m, 2H), 7.39 (s, 1H), 7.31-7.22 (m, 2H), 7.04-6.98 (m, 1H), 6.27 (s, 1H), 4.16 (t, J=1.0 Hz, 1H), 3.86 (s, 1H), 3.76 (s, 1H), 2.02 (s, 1H), 0.98 (s, 2H), 0.93 (s, 2H).

Compound 31: 3-(1H-benzimidazol-2-carbonyl)-4-(4-ethoxyphenyl)-5-isopropylspiro[inden-2,2'-pyrrolidine]-1,3-dione

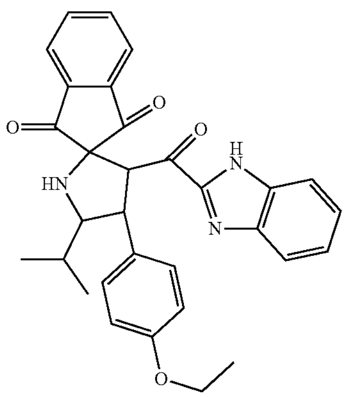 [SMILES: CCOc1ccc(C2C(C(C)C)NC3(C(=O)c4ccccc4C3=O)C2C(=O)c2nc3ccccc3[nH]2)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 450 mg (3 mmol) of 4-ethoxybenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 890 mg of a product: 1-benzimidazol-2-yl-3-(4-ethoxyphenyl)prop-2-en-1-one. 5 mL of absolute ethanol was added to a reaction flask, then 65 mg (0.56 mmol) of valine, 163 mg (0.56 mmol) of the 1-benzimidazol-2-yl-3-(4-ethoxyphenyl)prop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 94 mg of the final product: 3-(1H-benzimidazol-2-carbonyl)-4-(4-ethoxyphenyl)-5-isopropylspiro[inden-2,2'-pyrrolidine]-1,3-dione, and a melting point of the final product was measured by a micro melting point meter to be 203.0° C. to 207.1° C. $^1$H NMR (500 MHz, Chloroform-d): δ 8.01 (dd, J=5.6, 3.9 Hz, 2H), 7.92-7.82 (m, 3H), 7.55 (s, 1H), 7.37 (s, 1H), 7.27 (d, J=2.7 Hz, 2H), 7.12-7.06 (m, 2H), 6.95-6.89 (m, 2H), 4.23 (t, J=1.0 Hz, 1H), 3.97 (d, J=1.4 Hz, 2H), 3.86 (s, 1H), 3.80 (s, 1H), 2.02 (s, 1H), 1.41 (s, 2H), 0.88 (s, 2H), 0.83 (s, 2H).

Compound 32: 3-(1H-benzimidazol-2-carbonyl)-4-(4-bromophenyl)-5-isopropylspiro[inden-2,2'-pyrrolidine]-1,3-dione

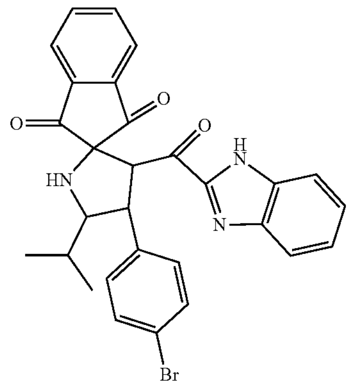 [SMILES: CC(C)C1NC2(C(=O)c3ccccc3C2=O)C(C(=O)c2nc3ccccc3[nH]2)C1c1ccc(Br)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 4-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-4-bromophenylprop-2-en-1-one. 5 mL of absolute ethanol was added to a reaction flask, then 65 mg (0.56 mmol) of valine, 183 mg (0.56 mmol) of the 1-benzimidazol-2-yl-4-bromophenylprop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 88 mg of the final product: 3-(1H-benzimidazol-2-carbonyl)-4-(4-bromophenyl)-5-isopropyl-spiro[inden-2,2'-pyrrolidine]-1,3-dione, and a melting point of the final product was measured by a micro melting point meter to be 244.0° C. to 246.5° C. $^1$H NMR (500 MHz, Chloroform-d): δ 8.07 (dd, J=5.7, 3.8 Hz, 3H), 7.90-7.82 (m, 4H), 7.57-7.51 (m, 4H), 7.39 (s, 1H), 7.26 (d, J=16.0 Hz, 2H), 7.18-7.12 (m, 3H), 4.23 (t, J=1.0 Hz, 1H), 3.86 (s, 1H), 3.76 (s, 1H), 2.02 (s, 1H), 0.95 (s, 3H), 0.89 (s, 3H).

Compound 33: 3-(1H-benzimidazol-2-carbonyl)-4-cyclohexyl-5-(methylthio)ethylspiro[inden-2,2'-pyrrolidine]-1,3-dione

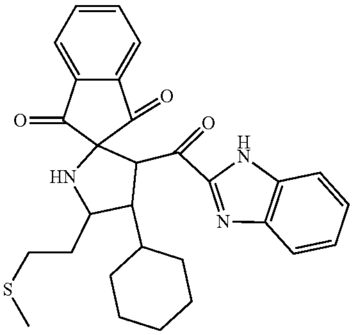 [SMILES: CSCCC1NC2(C(=O)c3ccccc3C2=O)C(C(=O)c2nc3ccccc3[nH]2)C1C1CCCCC1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 336 mg (3 mmol) of cyclohexanecarboxaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 580 mg of a product: 1-(1H-benzimidazol-2-yl)-3-cyclohexylprop-2-en-1-one. 142 mg (0.56 mmol) of the 1-(1H-benzimidazol-2-yl)-3-cyclohexylprop-2-en-1-one, 119 mg (0.67 mmol) of ninhydrin hydrate, and 84 mg (0.56 mmol) of methionine were weighed and added to a reaction flask, 5 mL of a methanol aqueous solution (methanol:water=10:1) was added to the reaction flask, and a reaction was allowed at room temperature for 2 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 110 mg of a yellow solid, and a melting point of the final product was measured by a micro melting point meter to be 213.4° C. to 215.9° C. $^1$H NMR (500 MHz, Chloroform-d): δ 8.07 (dd, J=5.7, 3.8 Hz, 3H), 7.90-7.82 (m, 4H), 7.53 (s, 1H), 7.39 (s, 1H), 7.21 (s, 1H), 7.06 (s, 1H), 3.80 (s, 1H), 3.34 (s, 1H), 2.72 (d, J=12.5 Hz, 1H), 2.59 (d, J=12.5 Hz, 1H), 2.22 (s, 1H), 2.15 (s, 3H), 1.87 (d, J=12.5 Hz, 1H), 1.81-1.75 (m, 2H), 1.57-1.33 (m, 12H).

Compound 34: 3-(1H-benzimidazol-2-carbonyl)-4-(4-chloro-3-fluorophenyl)-5-(2-methylthio)ethyl-spiro[inden-2,2'-pyrrolidine]-1,3-dione

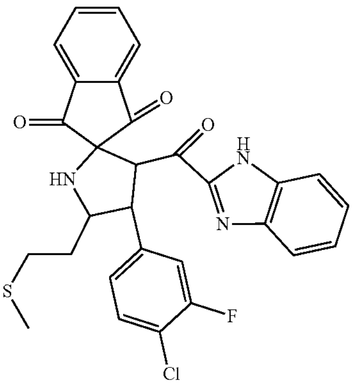 [SMILES: CSCCC1NC2(C(=O)c3ccccc3C2=O)C(C(=O)c2nc3ccccc3[nH]2)C1c1ccc(Cl)c(F)c1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 475 mg (3 mmol) of 3-fluoro-4-chlorobenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 823 mg of a product: (E)-1-(1H-benzo[d]imidazol-2-yl)-3-(3-fluoro-4-chlorophenyl)prop-2-en-1-one. 5 mL of a methanol solution ($MeOH:H_2O$=10:1) was first added to a reaction flask, then 168 mg (0.56 mmol) of the (E)-1-(1H-benzo[d]imidazol-2-yl)-3-(3-fluoro-4-chlorophenyl)prop-2-en-1-one, 119 mg (0.67 mmol) of ninhydrin hydrate, and 84 mg (0.56 mmol) of methionine were added successively to the reaction flask, and a reaction was allowed at room temperature for 8 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 105 mg of a yellow solid, and a melting point of the yellow solid was measured by a micro melting point meter to be 198.4° C. to 200.6° C. $^1$H NMR (500 MHz, Chloroform-d): δ 8.01 (dd, J=5.6, 3.9 Hz, 2H), 7.92-7.82 (m, 3H), 7.57-7.49 (m, 2H), 7.39 (s, 1H), 7.26 (d, J=2.3 Hz, 2H), 7.23-7.17 (m, 1H), 7.06 (s, 1H), 4.10 (t, J=1.0 Hz, 1H), 3.86 (s, 1H), 3.30 (s, 1H), 2.66-2.54 (m, 2H), 2.15 (s, 2H), 1.87 (d, J=2.9 Hz, 2H).

Compound 35: 3-(1H-benzimidazol-2-carbonyl)-4-(4-chlorophenyl)-5-(2-methylthio)ethylspiro[inden-2,2'-pyrrolidine]-1,3-dione

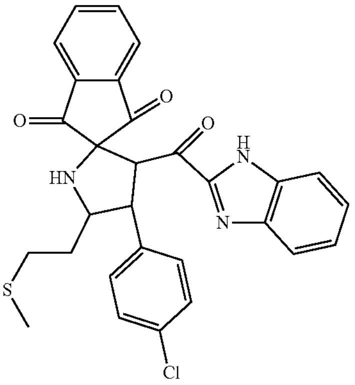 [SMILES: CSCCC1NC2(C(=O)c3ccccc3C2=O)C(C(=O)c2nc3ccccc3[nH]2)C1c1ccc(Cl)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 422 mg (3 mmol) of p-chlorobenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 751 mg of a product: (E)-1-(1H-benzo[d]imidazol-2-yl)-3-(4-chlorophenyl)prop-2-en-1-one. 5 mL of absolute ethanol was added to a reaction flask, then 84 mg (0.56 mmol) of methionine, 158 mg (0.56 mmol) of the (E)-1-(1H-benzo[d]imidazol-2-yl)-3-(4-chlorophenyl)prop-2-en-1-one, and 119 mg (0.67 mmol) of ninhydrin hydrate were added successively to the reaction flask, and a reaction was allowed for 8 h at room temperature under stirring to obtain a reaction solution; monitoring analysis was conducted by TLC (PE: EA=2:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was concentrated under vacuum to obtain 108 mg of a yellow solid product, and a melting point of the yellow solid was measured by a micro melting point meter to be 256.3° C. to 260.4° C. $^1H$ NMR (500 MHz, Chloroform-d): δ 8.01 (dd, J=5.6, 3.9 Hz, 2H), 7.90-7.82 (m, 3H), 7.56 (d, J=8.8 Hz, 2H), 7.43-7.35 (m, 3H), 7.28 (s, 1H), 7.26-7.19 (m, 2H), 4.10 (t, J=1.0 Hz, 1H), 3.86 (s, 1H), 3.30 (s, 1H), 2.60 (q, J=12.4 Hz, 2H), 2.15 (s, 2H), 1.94-1.83 (m, 2H).

Compound 36: 3-(1H-benzimidazol-2-carbonyl)-5-(2-methylthio)ethyl-4-p-tolylspiro[inden-2,2'-pyrrolidine]-1,3-dione

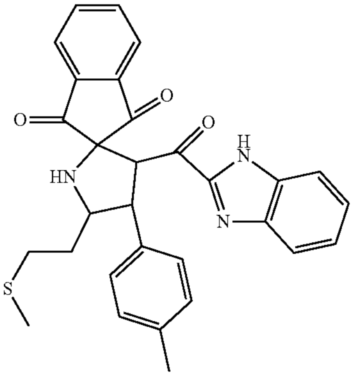 [SMILES: CSCCC1NC2(C(=O)c3ccccc3C2=O)C(C(=O)c2nc3ccccc3[nH]2)C1c1ccc(C)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 360 mg (3 mmol) of p-methylbenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 684 mg of a product: 1-(1H-benzimidazol-2-yl)-3-p-tolylprop-2-en-1-one. 147 mg (0.56 mmol) of the 1-(1H-benzimidazol-2-yl)-3-p-tolylprop-2-en-1-one, 119 mg (0.67 mmol) of ninhydrin hydrate, and 84 mg (0.56 mmol) of methionine were weighed, separately; 5 mL of a methanol aqueous solution ($MeOH:H_2O=10:1$) was first added to a reaction flask, then the weighed methionine, 1-(1H-benzimidazol-2-yl)-3-p-tolylprop-2-en-1-one, and ninhydrin hydrate were added successively to the reaction flask, and a reaction was allowed under reflux at 80° C. for 2 h to obtain a reaction solution; monitoring analysis was conducted by TLC (PE: EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 98 mg of a solid, and a melting point of the solid was measured by a micro melting point meter to be 260.1° C. to 262.8° C. $^1H$ NMR (500 MHz, Chloroform-d): δ 8.05 (dd, J=5.7, 3.8 Hz, 2H), 7.90-7.82 (m, 3H), 7.56 (d, J=8.8 Hz, 2H), 7.37 (s, 1H), 7.28 (s, 1H), 7.21-7.14 (m, 3H), 7.13-7.06 (m, 2H), 4.10 (t, J=1.0 Hz, 1H), 3.86 (s, 1H), 3.30 (s, 1H), 2.68 (d, J=12.4 Hz, 1H), 2.56 (d, J=12.4 Hz, 1H), 2.31 (t, J=1.0 Hz, 3H), 2.15 (s, 2H), 1.94 (d, J=12.2 Hz, 1H), 1.86 (d, J=12.3 Hz, 1H).

Compound 37: 3-(1H-benzimidazol-2-carbonyl)-3,4-diethoxyphenyl-5-(2-methylthio)ethylspiro[inden-2,2'-pyrrolidine]-1,3-dione

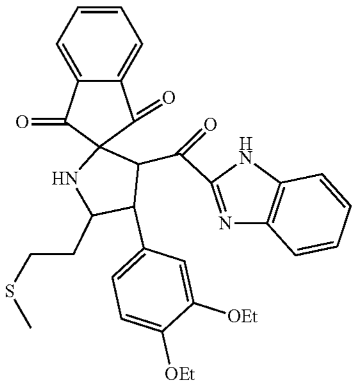 [SMILES: CCOc1ccc(C2C(CCSC)NC3(C(=O)c4ccccc4C3=O)C2C(=O)c2nc3ccccc3[nH]2)cc1OCC]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 582 mg (3 mmol) of 3,4-diethoxybenzaldehyde was added to the flask to allow a reaction for 8 h to obtain a reaction solution; monitoring analysis was conducted by TLC, and when a monitoring analysis result showed that the reaction was completed, the reaction solution was poured into a beaker;

an appropriate amount of distilled water was added to the beaker, and the beaker was allowed to stand to make a yellow solid precipitated; and the yellow solid was collected through suction filtration and dried to obtain 890 mg of a product: 1-(1H-benzimidazol-2-yl)-3-(3,4-diethoxyphenyl) prop-2-en-1-one. 5 mL of absolute ethanol was added to a reaction flask, then 84 mg (0.56 mmol) of methionine, 188 mg (0.56 mmol) of the 1-(1H-benzimidazol-2-yl)-3-(3,4-diethoxyphenyl)prop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 64 mg of the final product: 3-(1H-benzimidazol-2-carbonyl)-3,4-diethoxyphenyl-5-(2-methylthio)ethylspiro[inden-2,2'-pyrrolidine]-1,3-dione, and a melting point of the final product was measured by a micro melting point meter to be 140.4° C. to 143.8° C. $^1$H NMR (500 MHz, Chloroform-d): δ 8.01 (dd, J=5.6, 3.9 Hz, 2H), 7.90-7.82 (m, 3H), 7.54 (s, 1H), 7.38 (s, 1H), 7.27 (s, 1H), 7.00 (dd, J=1.9, 1.0 Hz, 1H), 6.95-6.89 (m, 1H), 6.84 (d, J=7.5 Hz, 1H), 6.30 (s, 1H), 4.12-3.98 (m, 6H), 3.86 (s, 1H), 3.30 (s, 1H), 2.60 (q, J=12.4 Hz, 2H), 2.15 (s, 3H), 1.84 (d, J=12.3 Hz, 1H), 1.70 (d, J=12.5 Hz, 1H), 1.40 (d, J=10.1 Hz, 7H).

Compound 38: 3-(1H-benzimidazol-2-carbonyl)-4-(3-bromophenyl)-5-(2-methylthio)ethylspiro[inden-2,2'-pyrrolidine]-1,3-dione

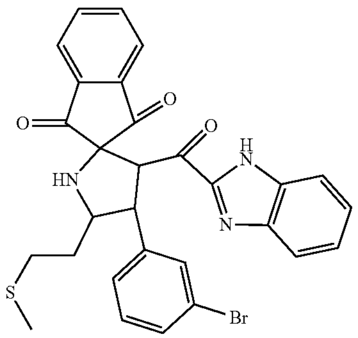 [SMILES: CSCCC1NC2(C(=O)c3ccccc3C2=O)C(C(=O)c2nc3ccccc3[nH]2)C1c1cccc(Br)c1]

540 mg (5 mmol) of o-phenylenediamine and 0.49 mL (6.5 mmol) of DL-lactic acid were taken and added to a round-bottom flask, then 2 mL of a mixture of hydrochloric acid and water (HCl:$H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 3-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-3-bromophenylprop-2-en-1-one. 5 mL of absolute ethanol was added to a reaction flask, then 84 mg (0.56 mmol) of methionine, 183 mg (0.56 mmol) of the 1-benzimidazol-2-yl-3-bromophenylprop-2-en-1-one, and 119 mg (0.67 mmol) of ninhydrin hydrate were added successively to the reaction flask, and a reaction was allowed at 80° C. for 8 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 75 mg of a yellow solid, and a melting point of the yellow solid was measured by a micro melting point meter to be 145.5° C. to 149.5° C. $^1$H NMR (500 MHz, Chloroform-d): δ 8.01 (dd, J=5.6, 3.9 Hz, 2H), 7.90-7.82 (m, 3H), 7.57 (s, 1H), 7.56-7.46 (m, 3H), 7.41-7.34 (m, 2H), 7.28 (s, 1H), 7.05-6.98 (m, 1H), 4.10 (t, J=1.0 Hz, 1H), 3.86 (s, 1H), 3.30 (s, 1H), 2.68 (d, J=12.5 Hz, 1H), 2.56 (d, J=12.5 Hz, 1H), 2.15 (s, 2H), 1.94-1.83 (m, 2H).

Compound 39: 3-(1H-benzimidazol-2-carbonyl)-4-(4-ethoxyphenyl)-5-(2-methylthio)ethylspiro[inden-2,2'-pyrrolidine]-1,3-dione

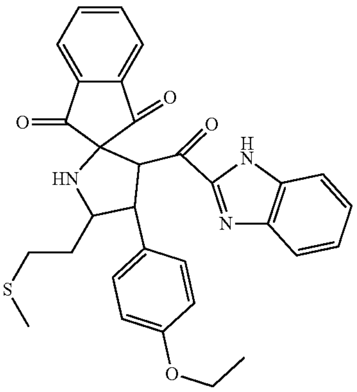 [SMILES: CCOc1ccc(C2C(CCSC)NC3(C(=O)c4ccccc4C3=O)C2C(=O)c2nc3ccccc3[nH]2)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 450 mg (3 mmol) of 4-ethoxybenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 890 mg of a product: 1-benzimidazol-2-yl-3-(4-ethoxyphenyl)prop-2-en-1-one. 5 mL of absolute ethanol was added to a reaction flask, then 84 mg (0.56 mmol) of methionine, 163 mg (0.56 mmol) of the 1-benzimidazol-2-yl-3-(4-ethoxyphenyl)prop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 94 mg of the final product: 3-(1H-benzimidazol-2-carbonyl)-4-(4-ethoxyphenyl)-5-(2-methylthio)ethylspiro[inden-2,2'-pyrrolidine]-1,3-dione, and a melting point of the final product was measured by a micro melting point meter to be 189.3° C. to 190.8° C. $^1H$ NMR (500 MHz, Chloroform-d): δ 8.01 (dd, J=5.6, 3.9 Hz, 2H), 7.92-7.82 (m, 3H), 7.56 (d, J=7.5 Hz, 2H), 7.37 (s, 1H), 7.27 (s, 1H), 7.12-7.06 (m, 2H), 6.95-6.89 (m, 2H), 4.03 (t, J=1.0 Hz, 1H), 3.97 (s, 2H), 3.79 (s, 1H), 3.30 (s, 1H), 2.62 (d, J=12.5 Hz, 1H), 2.57 (d, J=12.3 Hz, 1H), 2.15 (s, 2H), 1.90-1.80 (m, 2H), 1.41 (s, 2H).

Compound 40: 3-(1H-benzimidazol-2-carbonyl)-4-(4-bromophenyl)-5-(2-methylthio)ethylspiro[inden-2,2'-pyrrolidine]-1,3-dione

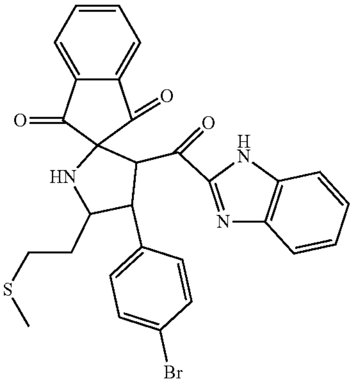

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 4-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-4-bromophenylprop-2-en-1-one. 5 mL of absolute ethanol was added to a reaction flask, then 84 mg (0.56 mmol) of methionine, 183 mg (0.56 mmol) of the 1-benzimidazol-2-yl-4-bromophenylprop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 78 mg of the final product: 3-(1H-benzimidazol-2-carbonyl)-4-(4-bromophenyl)-5-(2-methylthio)ethylspiro[inden-2,2'-pyrrolidine]-1,3-dione, and a melting point of the final product was measured by a micro melting point meter to be 156.5° C. to 160.4° C. $^1H$ NMR (500 MHz, Chloroform-d): δ 8.01 (dd, J=5.6, 3.9 Hz, 3H), 7.90-7.82 (m, 4H), 7.59-7.52 (m, 5H), 7.39 (s, 1H), 7.28 (s, 1H), 7.20-7.14 (m, 3H), 4.10 (t, J=1.0 Hz, 1H), 3.86 (s, 1H), 3.30 (s, 1H), 2.68 (d, J=12.5 Hz, 1H), 2.56 (d, J=12.5 Hz, 1H), 2.15 (s, 3H), 1.94-1.83 (m, 2H).

Compound 41: 3-(1H-benzimidazol-2-carbonyl)-4-cyclohexyl-5-(1H-indol-3-yl)spiro[inden-2,2'-pyrrolidine]-1,3-dione

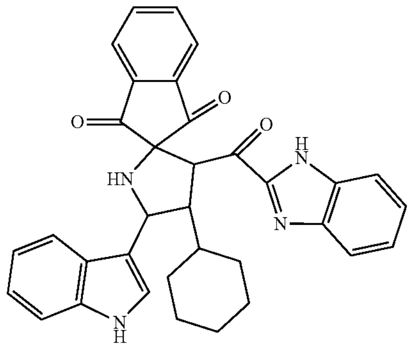 [SMILES: O=C(c1nc2ccccc2[nH]1)C1C(C2CCCCC2)C(c2c[nH]c3ccccc23)NC12C(=O)c1ccccc1C2=O]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 336 mg (3 mmol) of cyclohexanecarboxaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 580 mg of a product: 1-(1H-benzimidazol-2-yl)-3-cyclohexylprop-2-en-1-one. 142 mg (0.56 mmol) of the 1-(1H-benzimidazol-2-yl)-3-cyclohexylprop-2-en-1-one, 119 mg (0.67 mmol) of ninhydrin hydrate, and 114 mg (0.56 mmol) of tryptophan were weighed and added to a reaction flask, 5 mL of a methanol aqueous solution (methanol:water=10:1) was added to the reaction flask, and a reaction was allowed at room temperature for 2 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 101 mg of a yellow solid, and a melting point of the yellow solid was measured by a micro melting point meter to be 178.5° C. to 180.5° C. $^1$H NMR (500 MHz, Chloroform-d): δ 9.43 (s, 1H), 8.05-7.97 (m, 3H), 7.90-7.82 (m, 5H), 7.53 (s, 1H), 7.40-7.31 (m, 3H), 7.27 (s, 1H), 7.21 (s, 1H), 7.14 (s, 1H), 7.08 (s, 1H), 4.70 (s, 1H), 3.98 (s, 1H), 2.95 (s, 1H), 2.12 (s, 1H), 1.54 (d, J=13.0 Hz, 2H), 1.52-1.33 (m, 9H).

Compound 42: 3-(1H-benzimidazol-2-carbonyl)-4-(4-chloro-3-fluorophenyl)-5-(1H-indol-3-yl)spiro[inden-2,2'-pyrrolidine]-1,3-dione

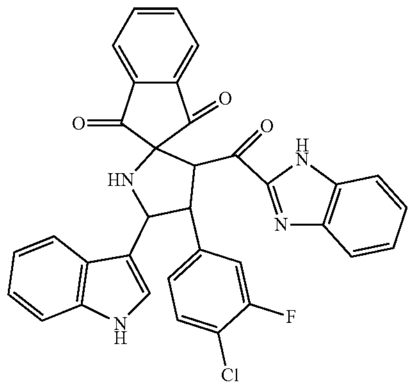 [SMILES: O=C(c1nc2ccccc2[nH]1)C1C(c2ccc(Cl)c(F)c2)C(c2c[nH]c3ccccc23)NC12C(=O)c1ccccc1C2=O]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 475 mg (3 mmol) of 3-fluoro-4-chlorobenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 823 mg of a product: (E)-1-(1H-benzo[d]imidazol-2-yl)-3-(3-fluoro-4-chlorophenyl)prop-2-en-1-one. 5 mL of a methanol solution ($MeOH:H_2O$=10:1) was first added to a reaction flask, then 168 mg (0.56 mmol) of the (E)-1-(1H-benzo[d]imidazol-2-yl)-3-(3-fluoro-4-chlorophenyl)prop-2-en-1-one, 119 mg (0.67 mmol) of ninhydrin hydrate, and 114 mg (0.56 mmol) of tryptophan were added successively to the reaction flask, and a reaction was allowed at room temperature for 8 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 103 mg of a yellow solid, and a melting point of the yellow solid was measured by a micro melting point meter to be 223.4° C. to 225.4° C. $^1$H NMR (500 MHz, Chloroform-d): δ 9.43 (s, 1H), 8.04-7.97 (m, 3H), 7.87 (d, J=13.2 Hz, 2H), 7.83-7.76 (m, 3H), 7.65 (s, 1H), 7.56-7.48 (m, 2H), 7.44-7.36 (m, 3H), 7.35 (s, 1H), 7.26-7.19 (m, 2H), 7.14 (s, 1H), 7.10 (s, 1H), 5.36 (s, 1H), 4.94 (t, J=1.0 Hz, 1H), 3.88 (s, 1H).

Compound 43: 3-(1H-benzimidazol-2-carbonyl)-4-(4-chlorophenyl)-5-(1H-indol-3-yl)spiro[inden-2,2'-pyrrolidi ne]-1,3-dione

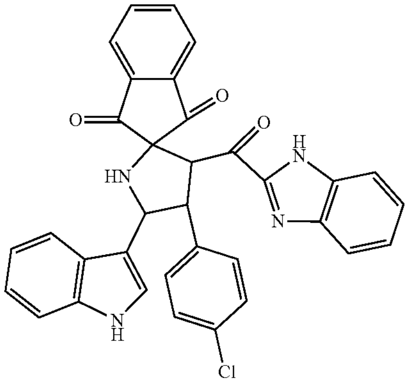 [SMILES: O=C(c1nc2ccccc2[nH]1)C1C(c2ccc(Cl)cc2)C(c2c[nH]c3ccccc23)NC12C(=O)c1ccccc1C2=O]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 422 mg (3 mmol) of p-chlorobenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 751 mg of a product: (E)-1-(1H-benzo[d]imidazol-2-yl)-3-(4-chlorophenyl)prop-2-en-1-one. 5 mL of absolute ethanol was added to a reaction flask, then 114 mg (0.56 mmol) of tryptophan, 158 mg (0.56 mmol) of the (E)-1-(1H-benzo[d]imidazol-2-yl)-3-(4-chlorophenyl)prop-2-en-1-one, and 119 mg (0.67 mmol) of ninhydrin hydrate were added successively to the reaction flask, and a reaction was allowed for 8 h at room temperature under stirring to obtain a reaction solution; monitoring analysis was conducted by TLC (PE:EA=2:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was concentrated under vacuum to obtain 108 mg of a yellow solid product, and a melting point of the yellow solid product was measured by a micro melting point meter to be 216.2° C. to 218.9° C. $^1H$ NMR (500 MHz, Chloroform-d): δ 9.43 (s, 1H), 8.05-7.97 (m, 3H), 7.90-7.76 (m, 6H), 7.55 (d, J=4.4 Hz, 3H), 7.45-7.33 (m, 5H), 7.28-7.21 (m, 4H), 7.14 (s, 1H), 7.10 (s, 1H), 5.32 (s, 1H), 4.94 (t, J=1.0 Hz, 1H), 3.88 (s, 1H).

Compound 44: 3-(1H-benzimidazol-2-carbonyl)-5-(1H-indol-3-yl)-4-p-tolylspiro[inden-2,2'-pyrrolidine]-1,3-dione

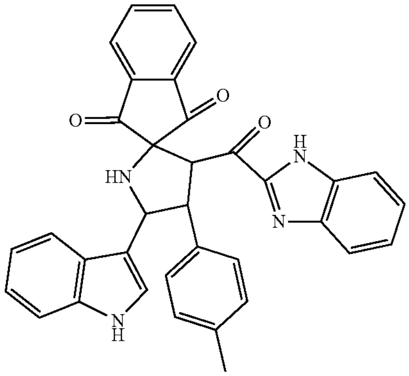 [SMILES: Cc1ccc(C2C(c3c[nH]c4ccccc34)NC3(C(=O)c4ccccc4C3=O)C2C(=O)c2nc3ccccc3[nH]2)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O$=1:2) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 360 mg (3 mmol) of p-methylbenzaldehyde was added to the flask to allow a reaction for 8 h to obtain a reaction solution; monitoring analysis was conducted by TLC (PE:EA=5:1), and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 684 mg of a product: 1-(1H-benzimidazol-2-yl)-3-p-tolylprop-2-en-1-one. 147 mg (0.56 mmol) of the 1-(1H-benzimidazol-2-yl)-3-p-tolylprop-2-en-1-one, 119 mg (0.67 mmol) of ninhydrin hydrate, and 114 mg (0.56 mmol) of tryptophan were weighed, separately; 5 mL of a methanol aqueous solution ($MeOH:H_2O=10:1$) was first added to a reaction flask, then the weighed tryptophan, 1-(1H-benzimidazol-2-yl)-3-p-tolylprop-2-en-1-one, and ninhydrin hydrate were added successively to the reaction flask, and a reaction was allowed under reflux at 80° C. for 2 h to obtain a reaction solution; monitoring analysis was conducted by TLC (PE:EA=3:1), and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 97 mg of a solid, and a melting point of the solid was measured by a micro melting point meter to be 156.1° C. to 160.5° C. $^1$H NMR (500 MHz, Chloroform-d): δ 9.43 (s, 1H), 8.05-7.97 (m, 3H), 7.90-7.76 (m, 5H), 7.65 (s, 1H), 7.56 (s, 1H), 7.36 (d, J=16.7 Hz, 2H), 7.25 (s, 1H), 7.18-7.07 (m, 7H), 5.29 (s, 1H), 4.94 (t, J=1.0 Hz, 1H), 3.90 (s, 1H), 2.31 (d, J=1.1 Hz, 3H).

Compound 45: 3-(1H-benzimidazol-2-carbonyl)-3,4-diethoxyphenyl-5-(1H-indol-3-yl)spiro[inden-2,2'-pyrrolidine]-1,3-dione

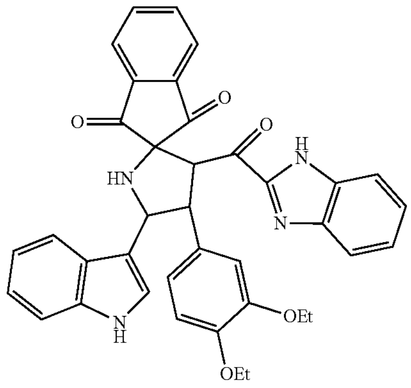 [SMILES: CCOc1ccc(C2C(c3c[nH]c4ccccc34)NC3(C(=O)c4ccccc4C3=O)C2C(=O)c2nc3ccccc3[nH]2)cc1OCC]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM:MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 582 mg (3 mmol) of 3,4-diethoxybenzaldehyde was added to the flask to allow a reaction for 8 h to obtain a reaction solution; monitoring analysis was conducted by TLC, and when a monitoring analysis result showed that the reaction was completed, the reaction solution was poured into a beaker;

an appropriate amount of distilled water was added to the beaker, and the beaker was allowed to stand to make a yellow solid precipitated; and the yellow solid was collected through suction filtration and dried to obtain 890 mg of a product: 1-(1H-benzimidazol-2-yl)-3-(3,4-diethoxyphenyl) prop-2-en-1-one. 5 mL of absolute ethanol was added to a reaction flask, then 114 mg (0.56 mmol) of tryptophan, 188 mg (0.56 mmol) of the 1-(1H-benzimidazol-2-yl)-3-(3,4-diethoxyphenyl)prop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 74 mg of the final product: 3-(1H-benzimidazol-2-carbonyl)-3,4-diethoxyphenyl-5-(1H-indol-3-yl)spiro[inden-2,2'-pyrrolidi ne]-1,3-dione, and a melting point of the final product was measured by a micro melting point meter to be 128.4° C. to 132.0° C. $^1H$ NMR (500 MHz, Chloroform-d): δ 9.43 (s, 1H), 8.04-7.97 (m, 3H), 7.87 (d, J=13.2 Hz, 2H), 7.83-7.76 (m, 3H), 7.62 (s, 1H), 7.54 (s, 1H), 7.42 (s, 1H), 7.32 (d, J=17.0 Hz, 2H), 7.24 (s, 1H), 7.14 (s, 1H), 7.10-7.04 (m, 2H), 7.03-6.97 (m, 1H), 6.88 (d, J=7.5 Hz, 1H), 5.27 (s, 1H), 4.94 (t, J=1.0 Hz, 1H), 4.12-4.01 (m, 4H), 3.88 (s, 1H), 1.40 (d, J=9.9 Hz, 6H).

Compound 46: 3-(1H-benzimidazol-2-carbonyl)-4-(3-bromophenyl)-5-(1H-indol-3-yl)spiro[inden-2,2'-pyrrolidine]-1,3-dione

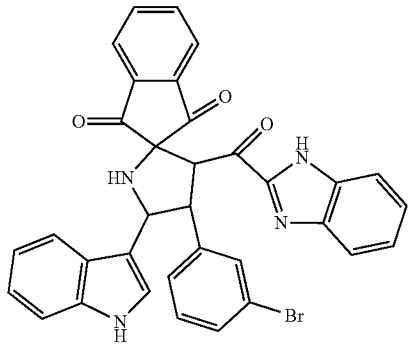 [SMILES: O=C(c1nc2ccccc2[nH]1)C1C(c2cccc(Br)c2)C(c2c[nH]c3ccccc23)NC12C(=O)c1ccccc1C2=O]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 3-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-3-bromophenylprop-2-en-1-one. 5 mL of absolute ethanol was added to a reaction flask, then 114 mg (0.56 mmol) of tryptophan, 183 mg (0.56 mmol) of the 1-benzimidazol-2-yl-3-bromophenylprop-2-en-1-one, and 119 mg (0.67 mmol) of ninhydrin hydrate were added successively to the reaction flask, and a reaction was allowed at 80° C. for 8 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 79 mg of a yellow solid, and a melting point of the yellow solid was measured by a micro melting point meter to be 201.2° C. to 204.5° C. $^1H$ NMR (500 MHz, Chloroform-d): δ 9.43 (s, 1H), 8.05-7.97 (m, 4H), 7.87 (d, J=13.2 Hz, 2H), 7.83-7.76 (m, 3H), 7.67-7.58 (m, 2H), 7.56-7.47 (m, 2H), 7.44-7.34 (m, 2H), 7.34 (d, J=5.7 Hz, 2H), 7.24 (s, 1H), 7.14 (s, 1H), 7.10-7.00 (m, 2H), 5.29 (s, 1H), 4.94 (t, J=1.0 Hz, 1H), 3.88 (s, 1H).

Compound 47: 3-(1H-benzimidazol-2-carbonyl)-4-(4-ethoxyphenyl)-5-isopropylspiro[inden-2,2'-pyrrolidine]-1,3-dione

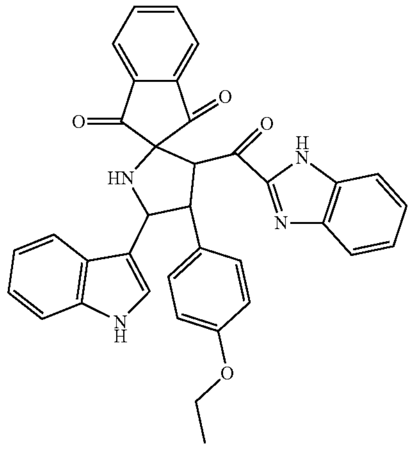 [SMILES: CCOc1ccc(C2C(c3c[nH]c4ccccc34)NC3(C(=O)c4ccccc4C3=O)C2C(=O)c2nc3ccccc3[nH]2)cc1]

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 450 mg (3 mmol) of 4-ethoxybenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 890 mg of a product: 1-benzimidazol-2-yl-3-(4-ethoxyphenyl)prop-2-en-1-one. 5 mL of absolute ethanol was added to a reaction flask, then 114 mg (0.56 mmol) of tryptophan, 163 mg (0.56 mmol) of the 1-benzimidazol-2-yl-3-(4-ethoxyphenyl)prop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 118 mg of the final product: 3-(1H-benzimidazol-2-carbonyl)-4-(4-ethoxyphenyl)-5-isopropylspiro[inden-2,2'-pyrrolidine]-1,3-dione, and a melting point of the final product was measured by a micro melting point meter to be 198.1° C. to 200.3° C. $^1H$ NMR (500 MHz, Chloroform-d): δ 9.43 (s, 1H), 8.05-7.97 (m, 4H), 7.90-7.76 (m, 6H), 7.55 (d, J=4.4 Hz, 3H), 7.38 (s, 1H), 7.33 (s, 1H), 7.26 (s, 1H), 7.13 (d, J=11.5 Hz, 2H), 7.08-7.02 (m, 3H), 6.96-6.90 (m, 3H), 5.36 (s, 1H), 4.94 (t, J=1.0 Hz, 1H), 3.97 (s, 2H), 3.88 (s, 1H), 1.36 (s, 3H).

Compound 48: 3-(1H-benzimidazol-2-carbonyl)-4-(4-bromophenyl)-5-isopropylspiro[inden-2,2'-pyrrolidine]-1,3-dione

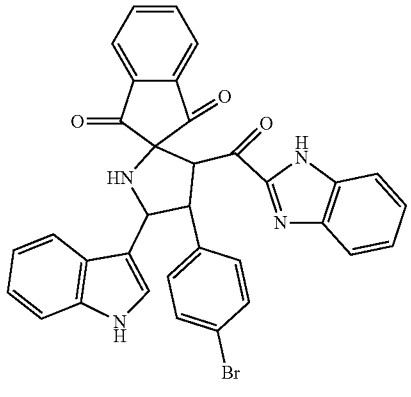

540 mg (5 mmol) of o-phenylenediamine and 0.49 mL (6.5 mmol) of DL-lactic acid were taken and added to a round-bottom flask, then 2 mL of a mixture of hydrochloric acid and water ($HCl:H_2O=1:2$) was added to the round-bottom flask, and a reaction under reflux was conducted at 80° C. for 4.5 h to obtain a reaction solution; when a TLC analysis result showed that the reaction was completed, an excess amount of a saturated $NaHCO_3$ aqueous solution was added to the reaction solution, and the round-bottom flask was allowed to stand for a while to make a white floccus precipitated; and the white floccus was collected through suction filtration, then dried, and weighed to obtain 700 mg of a white solid: 2-(α-hydroxy)ethylbenzimidazole. 648 mg (4 mmol) of the 2-(α-hydroxy)ethylbenzimidazole was weighed and dissolved in 8 mL of glacial acetic acid to obtain a 2-(α-hydroxy)ethylbenzimidazole solution, the 2-(α-hydroxy)ethylbenzimidazole solution was stirred at 85° C. for 5 min, then a chromium trioxide aqueous solution was slowly added dropwise (400 mg (4 mmol) of a chromium trioxide solid was dissolved with a small amount of distilled water in advance) to the 2-(α-hydroxy)ethylbenzimidazole solution to obtain a reaction system, and the reaction system was stirred at 85° C. to allow a reaction under reflux for 15 min to obtain a reaction solution; monitoring analysis was conducted by TLC (DCM: MeOH=20:1), and when a monitoring analysis result showed that the reaction was completed and a product was pure, the reaction solution was poured into an appropriate amount of ice water; extraction was conducted three times with ethyl acetate, and then back-extraction was conducted with a saturated NaCl aqueous solution; and a collected organic phase was spin-dried and weighed to obtain 610 mg of a yellow-brown solid: 2-acetylbenzimidazole. 480 mg (3 mmol) of the 2-acetylbenzimidazole was weighed and added to a flask, and dissolved with 10 mL of absolute ethanol; then 216 mg (5.4 mmol) of a NaOH solid was weighed and dissolved with a small amount of distilled water to obtain a NaOH solution; the NaOH solution was slowly added to the flask to obtain a mixed solution, and the mixed solution was stirred at room temperature for 5 min to 10 min; then 555 mg (3 mmol) of 4-bromobenzaldehyde was added to the flask to allow a reaction for 8 h to obtain a reaction solution; monitoring analysis was conducted by TLC, and when a monitoring analysis result showed that the reaction was completed, the reaction solution was poured into a beaker; an appropriate amount of distilled water was added to the beaker, and the beaker was allowed to stand to make a yellow solid precipitated; and the yellow solid was collected through suction filtration and dried to obtain 790 mg of a product: 1-benzimidazol-2-yl-4-bromophenylprop-2-en-1-one. 5 mL of absolute ethanol was added to a reaction flask, then 114 mg (0.56 mmol) of tryptophan, 183 mg (0.56 mmol) of the 1-benzimidazol-2-yl-4-bromophenylprop-2-en-1-one, and 119 mg (0.67 mmol) of ninhydrin hydrate were added successively to the reaction flask, and a reaction was allowed at 80° C. for 2 h to obtain a reaction solution; monitoring analysis was conducted by TLC, and when a monitoring analysis result showed that the reaction was completed, the reaction solution was spin-dried to obtain a spin-dried product; an appropriate amount of a column chromatography silica gel was weighed and prepared into a silica gel sand, and the spin-dried product was purified by a rapid preparative chromatograph with the silica gel sand to obtain a purified product, where the whole purification process was monitored by TLC; and the purified product was collected and spin-dried to obtain 78 mg of the final product: 3-(1H-benzimidazol-2-carbonyl)-4-(4-bromophenyl)-5-isopropylspiro[inden-2,2'-pyrrolidine]-1,3-dione, and a melting point of the final product was measured by a micro melting point meter to be 167.5° C. to 169.5° C. $^1$H NMR (500 MHz, Chloroform-d): δ 9.43 (s, 1H), 8.05-7.97 (m, 3H), 7.90-7.79 (m, 3H), 7.82-7.76 (m, 3H), 7.65 (s, 1H), 7.57-7.51 (m, 3H), 7.34 (d, J=5.6 Hz, 2H), 7.24 (s, 1H), 7.21-7.12 (m, 3H), 7.08 (s, 1H), 5.32 (s, 1H), 4.94 (t, J=1.0 Hz, 1H), 3.88 (s, 1H).

Example 2

1. Cell Lines

Human liver tumor cells HepG2, human colon cancer cells HCT116, and human gastric adenocarcinoma cells AGS were purchased from the Institute of Basic Medical Sciences, Chinese Academy of Medical Sciences. The cells each were preserved and passaged in the laboratory of the present disclosure according to respective cultivation data. Each cell line was routinely inoculated in a 50 mL cell culture flask, and cultivated with a 10% fetal bovine serum-containing DMEM/IRP-1640 medium at 37° C., 5% $CO_2$, and 100% humidity, where the medium was changed daily. When growing to a confluency of 80% to 90%, cells were digested with a mixture of trypsin and EDTA and passaged according to 1:3.

2. Experimental Method

An in vitro cell activity and proliferation inhibition experiment was conducted by an MTT method to investigate an impact of a target compound on a survival activity of each cell. Cells at a logarithmic growth phase were inoculated at $5\times10^3$ cells (100 μL)/well in a 96-well culture plate and cultivated for 24 h, and then compound solutions with different concentrations prepared in advance were added (100 μL) to the plate. At least 3 replicate wells were set for each concentration. A solvent control group without a compound and a blank control group without a cell were set. Edge wells each were filled with 200 μL of sterilized water. After 48 h of a contact between a compound and a cell, 20 μL of MTT (which had a concentration of 5 mg/mL, and was prepared with PBS, filtered, dispensed, and stored at −20° C.) was added to each well, and the plate was incubated at 37° C. and 5% $CO_2$ for 4 h. A liquid in each well was completely removed carefully, 150 μL of DMSO was added to each well, the plate was gently shaken on a microshaker for 10 min to make a purple crystal fully dissolved, and then an absorbance value was determined at 570 nm by a microplate reader. With a cell viability of the solvent control group without a compound as 100%, a cell survival rate was calculated as follows: a cell survival rate=(an absorbance value of a compound group−an absorbance value of the blank control group)/(an absorbance value of the control group−an absorbance value of the blank control group)× 100%. A half-maximal inhibitory concentration ($IC_{50}$) of a compound for a cell was calculated by the Graphpad Prism 5 software.

3. Experimental Results $IC_{50}$ values of inhibition of the compounds 1 to 48 and a positive drug on proliferation of tumor cells are shown in Table 1.

TABLE 1

$IC_{50}$ values of inhibition of the compounds 1 to 48 and a positive drug on proliferation of tumor cells

| | Antiproliferative activity ($IC_{50}$, μM) | | |
|---|---|---|---|
| Compound | HepG2 | HCT116 | AGS |
| 1 | >100 | >100 | 40.82 |
| 2 | >100 | >100 | >100 |
| 3 | >100 | 26.24 | 30.01 |
| 4 | >100 | 54.22 | 17.11 |
| 5 | 80.74 | 17.44 | 36.88 |
| 6 | 11.68 | 6.639 | 3.995 |
| 7 | 20.53 | 7.992 | 7.726 |
| 8 | >100 | 17.42 | 25.67 |
| 9 | >100 | 20.32 | 69.01 |
| 10 | 87.71 | 15.72 | 46.71 |
| 11 | >100 | 30.30 | >100 |

TABLE 1-continued

| IC$_{50}$ values of inhibition of the compounds 1 to 48 and a positive drug on proliferation of tumor cells | | | |
|---|---|---|---|
| | Antiproliferative activity (IC$_{50}$, μM) | | |
| Compound | HepG2 | HCT116 | AGS |
| 12 | >100 | 14.13 | 42.71 |
| 13 | >100 | >100 | >100 |
| 14 | 11.67 | 5.875 | 7.918 |
| 15 | >100 | 28.81 | 85.67 |
| 16 | 49.73 | 10.79 | 20.86 |
| 17 | 16.23 | 11.05 | 14.74 |
| 18 | >100 | >100 | >100 |
| 19 | >100 | 42.05 | 87.46 |
| 20 | >100 | 51.33 | 94.02 |
| 21 | 41.28 | 35.47 | 33.78 |
| 22 | 3.45 | 5.67 | 4.78 |
| 23 | 8.78 | 9.67 | 45.78 |
| 24 | 67.78 | 45.78 | 3.67 |
| 25 | 9.67 | 5.67 | 12.43 |
| 26 | >100 | 78.98 | 59.98 |
| 27 | >100 | >100 | 90.12 |
| 28 | 3.45 | 4.56 | 2.98 |
| 29 | 44.56 | 53.21 | 67.12 |
| 30 | 2.34 | 3.42 | 2.98 |
| 31 | 44.56 | 56.35 | 59.87 |
| 32 | 66.67 | >100 | >100 |
| 33 | 12.45 | 15.45 | 9.77 |
| 34 | 36.56 | 44.67 | 39.67 |
| 35 | 40.45 | 42.67 | 45.78 |
| 36 | 13.45 | 15.45 | 9.78 |
| 37 | >100 | >100 | 78.56 |
| 38 | 49.78 | 47.36 | 40.89 |
| 39 | >100 | >100 | >100 |
| 40 | 9.56 | 56.67 | 66.23 |
| 41 | 89.56 | 77.36 | 82.34 |
| 42 | 3.45 | 4.78 | 3.01 |
| 43 | 34.56 | 55.54 | 39.67 |
| 44 | 5.67 | 5.34 | 6.02 |
| 45 | >100 | 56.37 | >100 |
| 46 | 12.21 | 18.45 | 21.43 |
| 47 | 34.56 | 39.78 | 38.00 |
| 48 | 40.25 | 37.78 | 44.21 |
| Cisplatin | 43.20 | 39.07 | 46.01 |
| Nutlin-3a | 10.97 | 21.71 | 21.44 |

Activity test results show that most of the compounds to 48 have a significant antiproliferative activity for human liver tumor cells HepG2, human colon cancer cells HCT116, and/or human gastric adenocarcinoma cells AGS, and most of the compounds exhibit a stronger antiproliferative activity than cisplatin and/or Nutlin-3a. Therefore, the compounds 1 to 48 have a prospect of being developed into antitumor drugs.

What is claimed is:

1. A benzimidazole heteroatom-containing spiro compound with the following chemical structure or a pharmaceutically acceptable salt of the benzimidazole heteroatom-containing spiro compound:

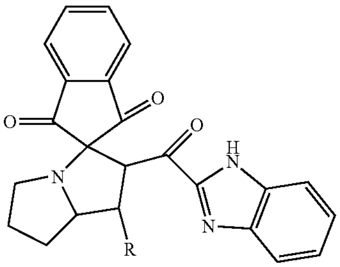

-continued

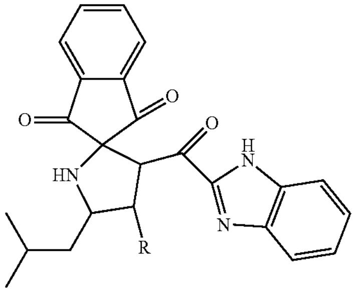

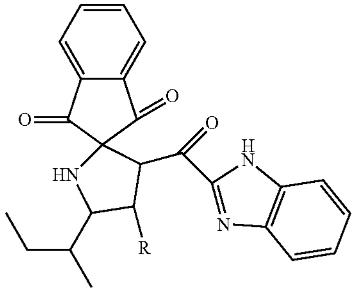

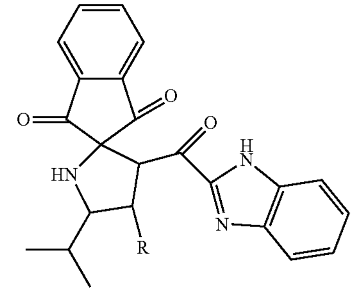

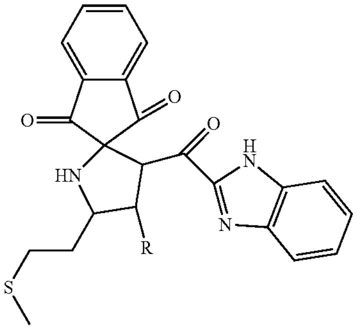

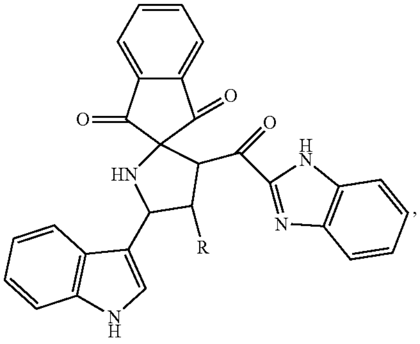

, wherein R is selected from the following structures:

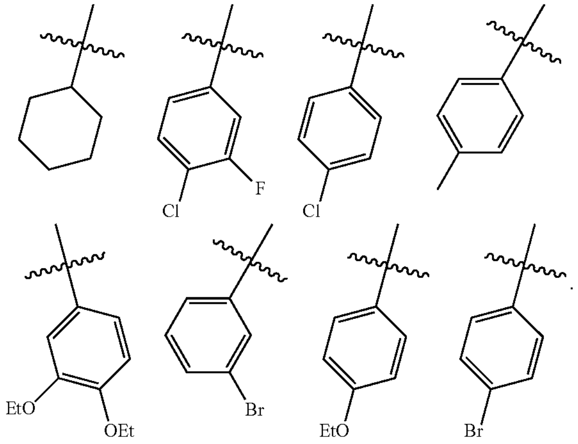

2. A method of treating a tumor, comprising orally administrating or injecting a drug to a tumor patient, wherein an active ingredient of the drug is the benzimidazole heteroatom-containing spiro compound or the pharmaceutically acceptable salt of the benzimidazole heteroatom-containing spiro compound according to claim 1.

3. The method according to claim 2, wherein the tumor is a liver cancer.

4. The method according to claim 2, wherein the tumor is a colon cancer.

5. The method according to claim 2, wherein the tumor is a gastric cancer.

* * * * *